US011950789B2

United States Patent
Lynch et al.

(10) Patent No.: US 11,950,789 B2
(45) Date of Patent: Apr. 9, 2024

(54) BONE CLEANING ASSEMBLY

(71) Applicant: Stryker Corporation, Kalamazoo, MI (US)

(72) Inventors: Robert E. Lynch, Portage, MI (US); Eric K. Diehl, San Francisco, CA (US); John Coleman Horton, IV, Austin, TX (US); Cyril A. Keilers, Georgetown, TX (US); John P. Bernero, Round Rock, TX (US)

(73) Assignee: Stryker Corporation, Kalamazoo, MI (US)

( * ) Notice: Subject to any disclaimer, the term of this patent is extended or adjusted under 35 U.S.C. 154(b) by 654 days.

(21) Appl. No.: 17/068,261

(22) Filed: Oct. 12, 2020

(65) Prior Publication Data

US 2021/0022751 A1 Jan. 28, 2021

Related U.S. Application Data

(60) Continuation of application No. 16/018,660, filed on Jun. 26, 2018, now Pat. No. 10,828,048, which is a
(Continued)

(51) Int. Cl.
*A61F 2/46* (2006.01)
*A61B 17/16* (2006.01)

(52) U.S. Cl.
CPC ........ *A61B 17/1635* (2013.01); *A61F 2/4644* (2013.01); *A61F 2002/4646* (2013.01)

(58) Field of Classification Search
CPC ..... A61F 2002/4646; A61F 2002/4645; A22C 17/04; A22C 17/004
See application file for complete search history.

(56) References Cited

U.S. PATENT DOCUMENTS 2,520,982 A * 9/1950 Urschel ................... B02C 18/00
425/436 R
2,542,426 A * 2/1951 Schoenberg ........... A22C 17/04
30/287
(Continued)

FOREIGN PATENT DOCUMENTS

EP 1226785 A1 7/2002
JP H07502442 A 3/1995
(Continued)

OTHER PUBLICATIONS

English language abstract and machine-assisted English translation for JP 2008-534191 extracted from espacenet.com database on Dec. 11, 2017, 20 pages.
(Continued)

*Primary Examiner* — David W Bates
(74) *Attorney, Agent, or Firm* — Howard & Howard Attorneys PLLC

(57) ABSTRACT

A cleaning module for cleaning bone stock used in surgical procedures. The cleaning module includes a shell. The shell defines a void space to receive the bone stock. A cutter is rotating mounted in the void space. A shaving tube, also able to rotate, is coaxially disposed about the cutter. The cutter and shaving tube have complementary edges. A drive assembly rotates the cutter and shaving tube at different speeds, at different times or in different directions relative to the cutter. As a result of the rotation of the cutter and shaving tube soft tissue adhering to the bone stock is cut away from the bone stock by the relative rotating of the cutting edges of the cutter and shaving tube.

18 Claims, 43 Drawing Sheets

Related U.S. Application Data continuation of application No. 15/627,488, filed on Jun. 20, 2017, now Pat. No. 10,034,673, which is a division of application No. 14/311,674, filed on Jun. 23, 2014, now Pat. No. 9,687,361, which is a continuation of application No. PCT/US2012/072160, filed on Dec. 28, 2012.

(60) Provisional application No. 61/581,310, filed on Dec. 29, 2011.

(56) References Cited

U.S. PATENT DOCUMENTS

| | | | |
|---|---|---|---|
| 3,739,994 A * | 6/1973 | McFarland | A22C 17/04 426/480 |
| 3,741,772 A * | 6/1973 | McFarland | A22C 17/04 426/480 |
| 3,896,522 A | 7/1975 | Lapeyre | |
| 4,069,980 A * | 1/1978 | Yarem | A22C 17/04 241/74 |
| 4,186,216 A | 1/1980 | Roth | |
| 4,629,131 A | 12/1986 | Podell | |
| 4,741,482 A | 5/1988 | Coggiola et al. | |
| 4,767,069 A | 8/1988 | Kim | |
| 5,580,305 A * | 12/1996 | McFarland | B02C 18/301 241/74 |
| 5,813,909 A * | 9/1998 | Goldston | A22C 17/04 452/138 |
| 5,836,528 A | 11/1998 | Hilgarth | |
| 5,906,322 A | 5/1999 | Hama | |
| 5,977,432 A | 11/1999 | Wolfinbarger, Jr. et al. | |
| D440,462 S * | 4/2001 | Johnson | D7/372 |
| 6,287,312 B1 | 9/2001 | Clokie et al. | |
| 6,824,087 B2 | 11/2004 | McPherson et al. | |
| 7,028,930 B2 | 4/2006 | Carnevale | |
| 7,063,283 B2 | 6/2006 | Wanat | |
| 7,131,605 B2 | 11/2006 | McPherson et al. | |
| 7,520,453 B2 | 4/2009 | Clapp et al. | |
| 8,002,774 B2 | 8/2011 | Burmeister, III et al. | |
| 8,512,342 B2 | 8/2013 | Meredith | |
| 8,622,953 B2 | 1/2014 | Hynes et al. | |
| 8,740,114 B2 | 6/2014 | Koltz et al. | |
| 8,951,101 B2 * | 2/2015 | Smith | A22C 17/004 452/138 |
| 9,107,426 B2 * | 8/2015 | Eisiminger | A22C 21/0069 |
| 9,687,361 B2 | 6/2017 | Diehl et al. | |
| 10,034,673 B2 | 7/2018 | Lynch et al. | |
| 2002/0176320 A1 | 11/2002 | Wulf et al. | |
| 2004/0155132 A1 | 8/2004 | McPherson et al. | |
| 2006/0261685 A1 | 11/2006 | Schindler et al. | |
| 2007/0270771 A1 * | 11/2007 | Ralph | A61F 2/4644 604/317 |
| 2009/0118713 A1 | 5/2009 | Munson | |
| 2009/0118735 A1 * | 5/2009 | Burmeister, III | A61F 2/4644 606/169 |
| 2010/0308142 A1 | 12/2010 | Krasznai et al. | |
| 2011/0166503 A1 * | 7/2011 | Koltz | A22C 17/04 606/167 |
| 2011/0248108 A1 | 10/2011 | Carriere | |
| 2012/0310243 A1 * | 12/2012 | Stratton | A61F 2/4644 606/79 |
| 2013/0001340 A1 | 1/2013 | Garcia et al. | |
| 2014/0263778 A1 | 9/2014 | Koltz et al. | |
| 2014/0303623 A1 | 10/2014 | Diehl et al. | |
| 2014/0322411 A1 | 10/2014 | Segurola et al. | |
| 2015/0201630 A1 * | 7/2015 | Hancock | A22C 17/04 29/428 |
| 2015/0313615 A1 * | 11/2015 | Jacobson | A61B 17/1659 606/85 |
| 2016/0309960 A1 | 10/2016 | Kolar et al. | |
| 2018/0020875 A1 | 1/2018 | Kolar et al. | |
| 2018/0078094 A1 | 3/2018 | Haney et al. | |
| 2018/0303494 A1 | 10/2018 | Lynch et al. | |
| 2019/0000275 A1 | 1/2019 | Sapire | |
| 2021/0022751 A1 * | 1/2021 | Lynch | A61F 2/4644 |

FOREIGN PATENT DOCUMENTS

| | | |
|---|---|---|
| JP | 2008534191 A | 8/2008 |
| WO | 9312731 A1 | 7/1993 |
| WO | 03017913 A1 | 3/2003 |
| WO | 2006105950 A2 | 10/2006 |
| WO | 2009061728 A1 | 5/2009 |
| WO | 2011057088 A1 | 5/2011 |

OTHER PUBLICATIONS

English language abstract for JPH 07-502442 extracted from espacenet.com database on Aug. 7, 2018, 1 page.
Marshall Excelsior Company, "LP Gas & Anhydrous Ammonia Equipment Manufacturer Product Brochure", 2009, pp. 1-72.
PCT "International Search Report and Written Opinion" for PCT/US2012/072160, dated Jul. 10, 2013.

* cited by examiner

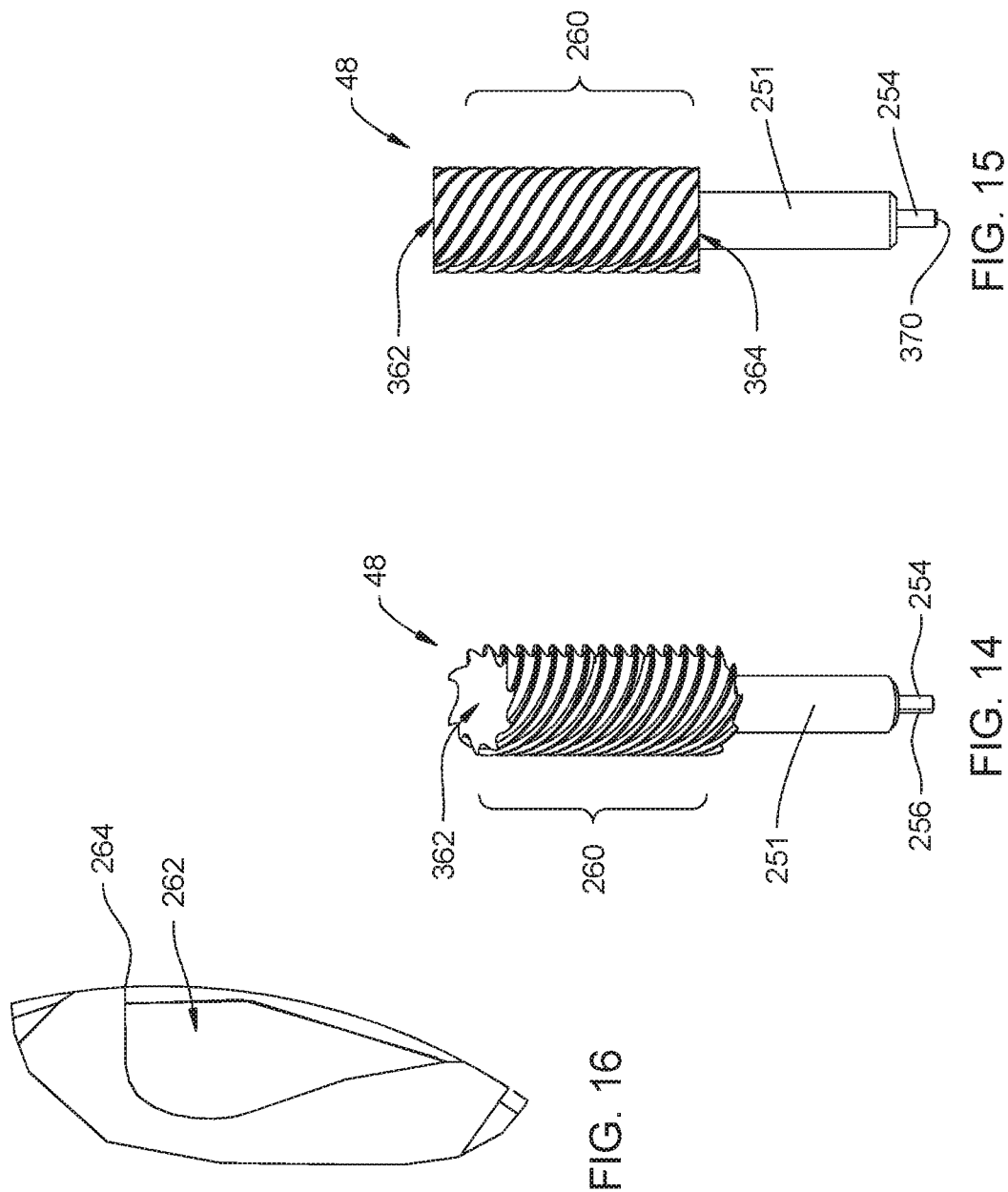

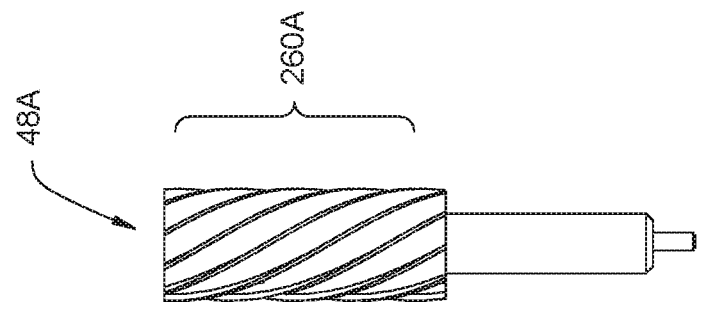
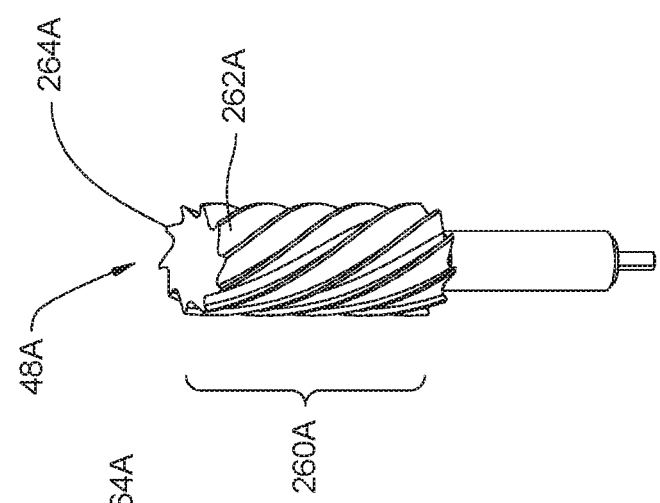
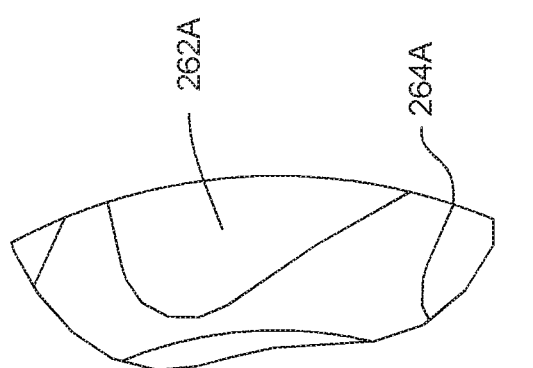

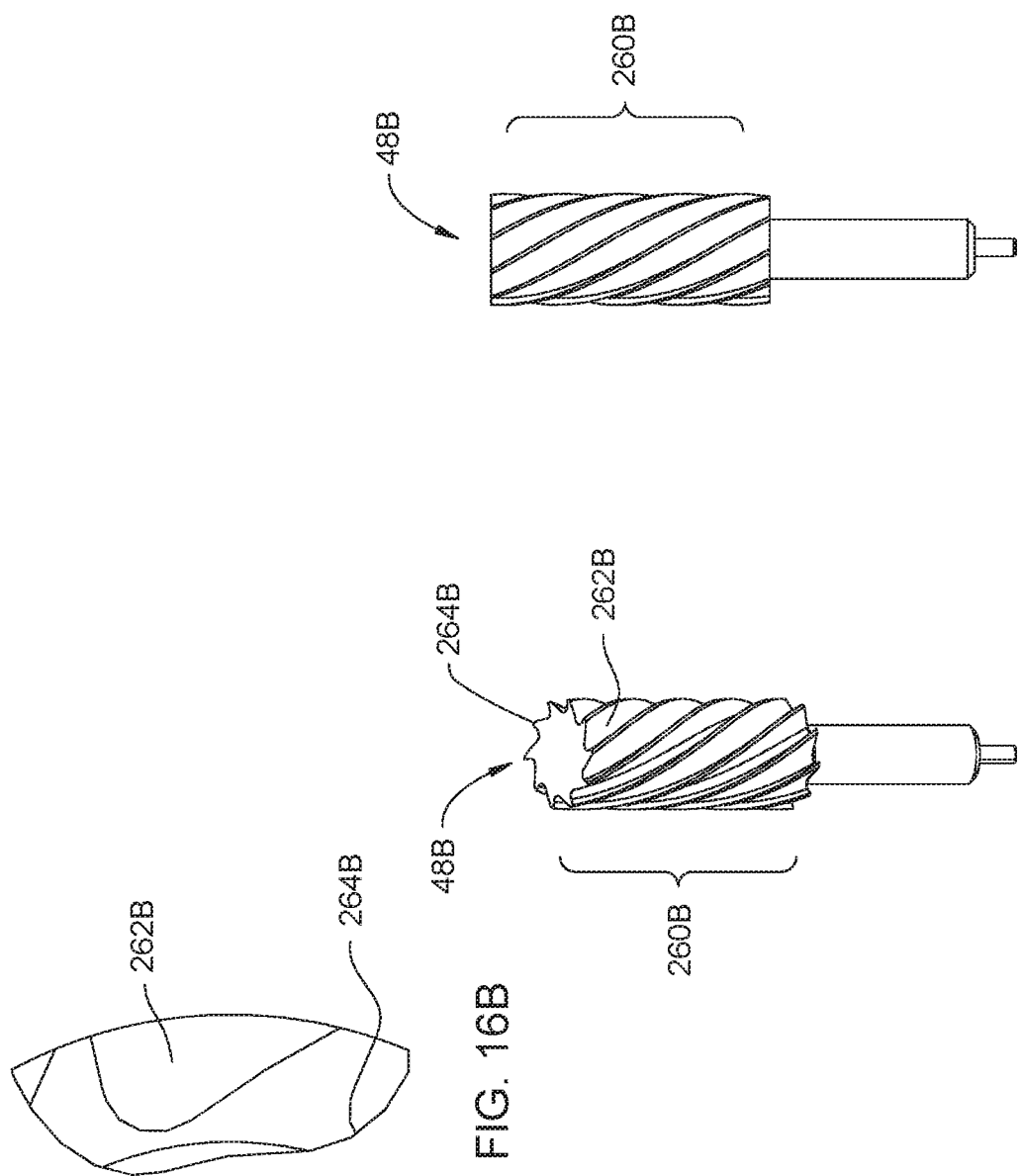

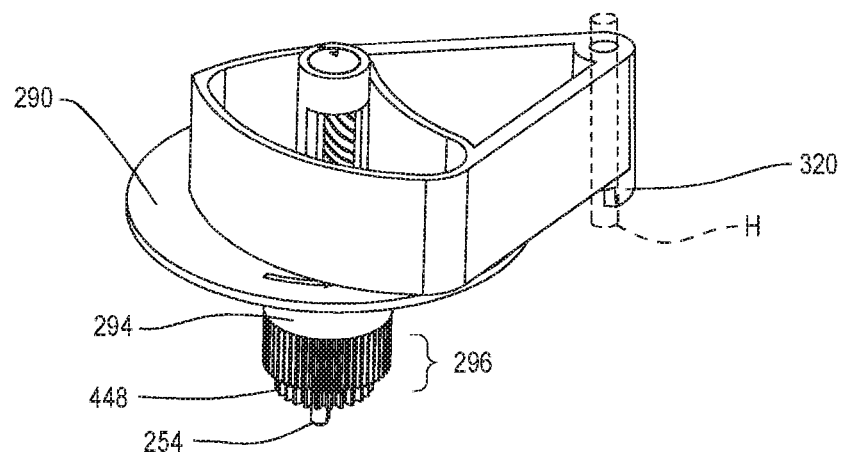
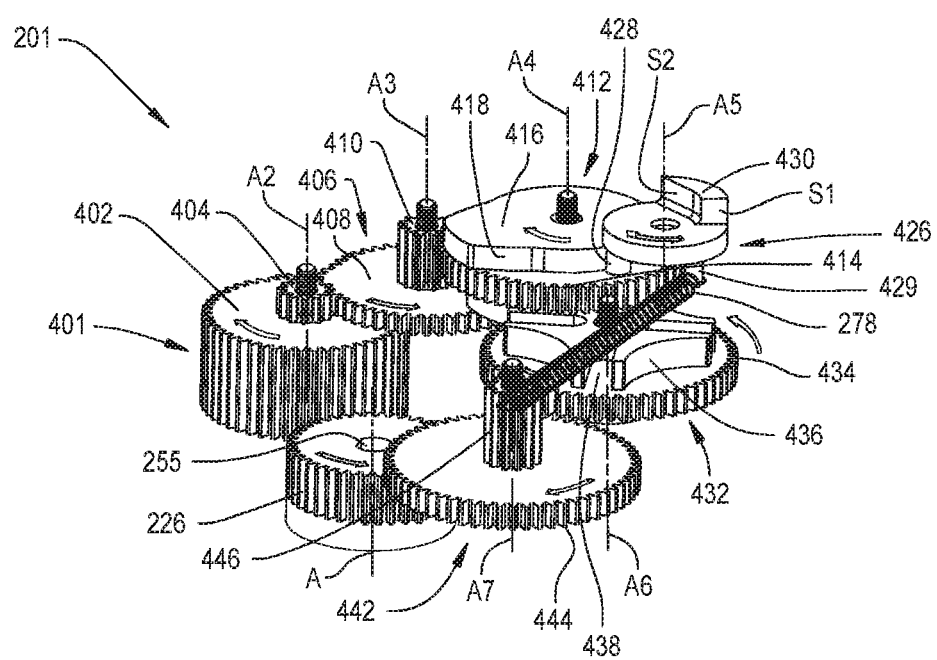
FIG. 22

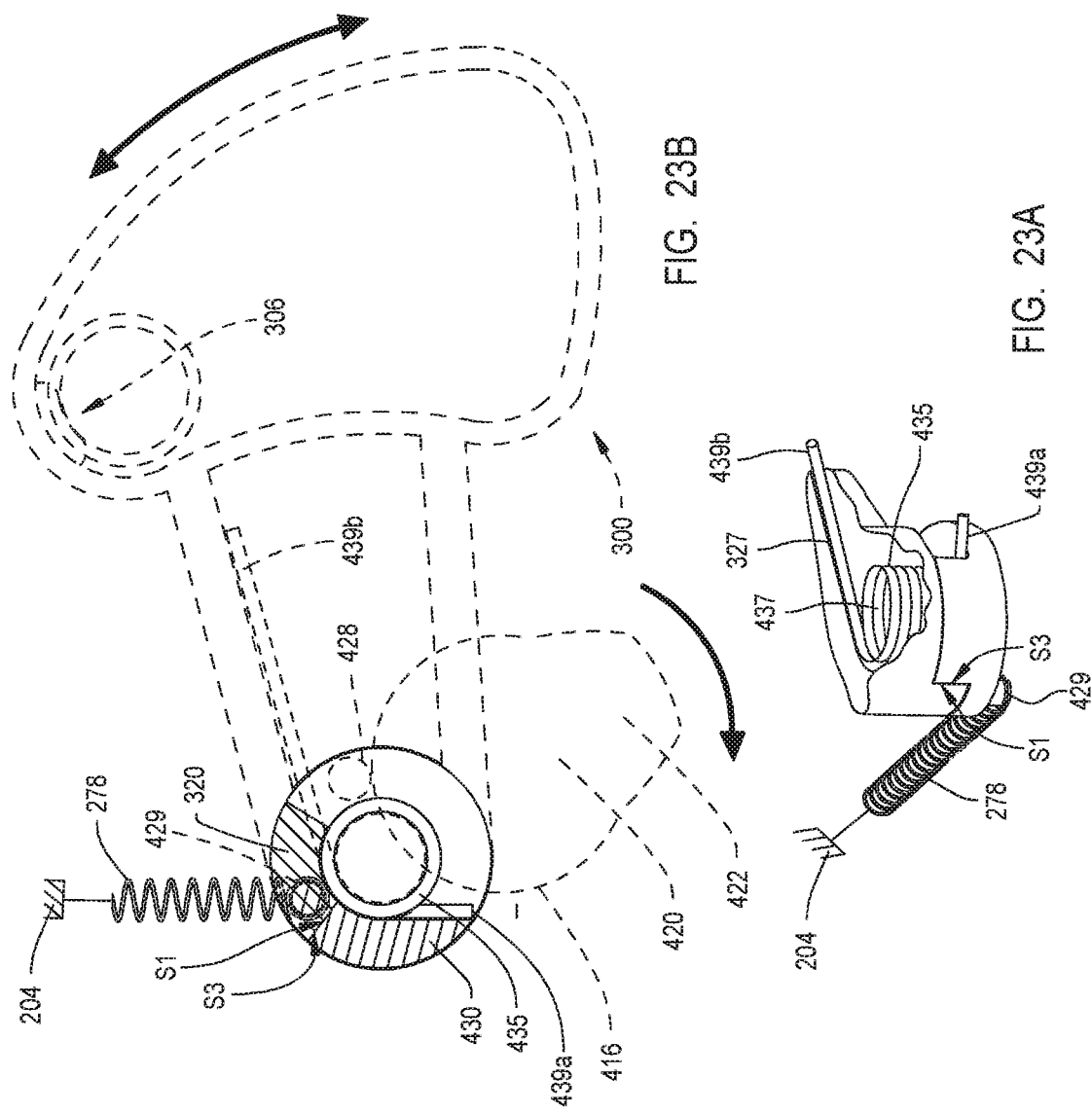

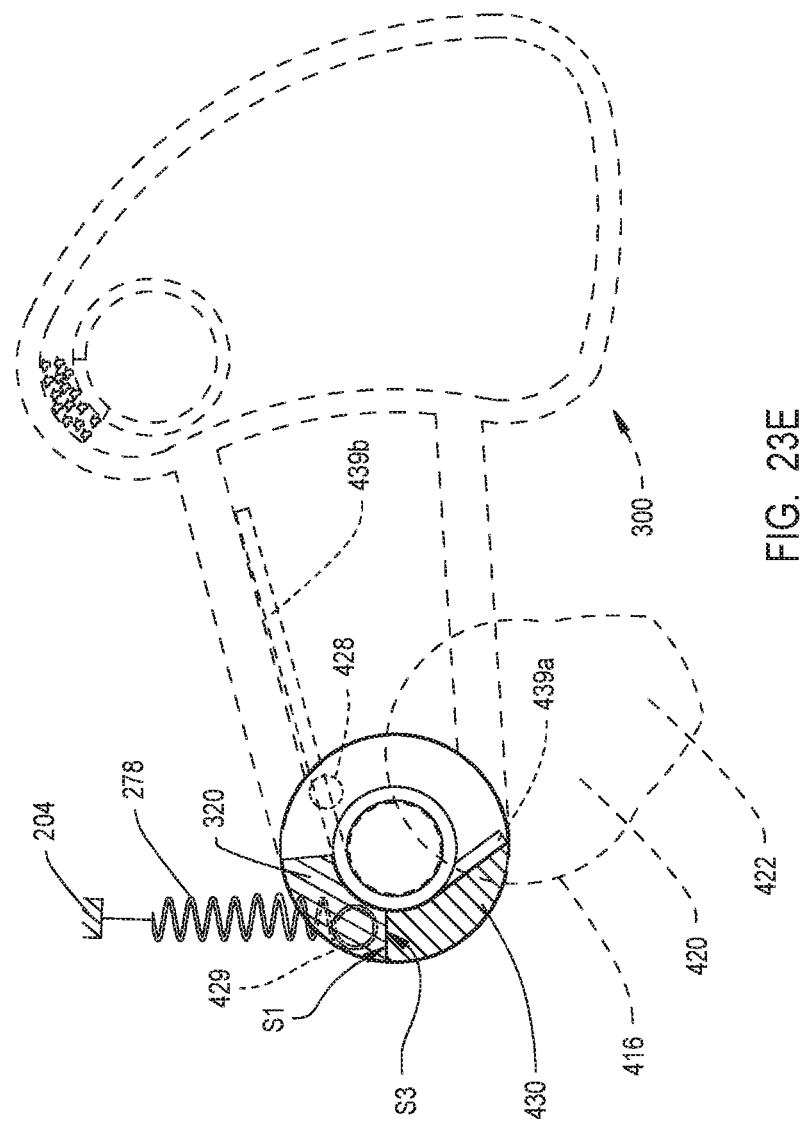

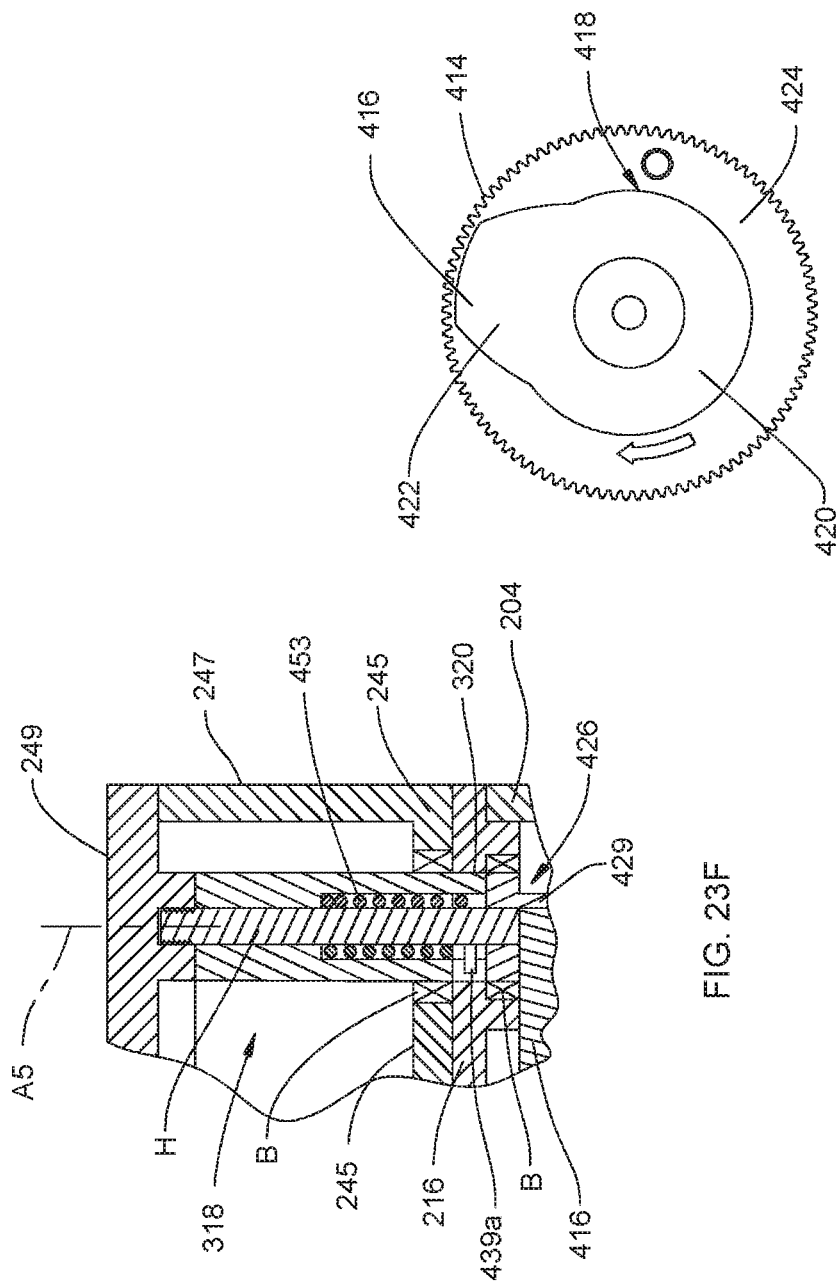

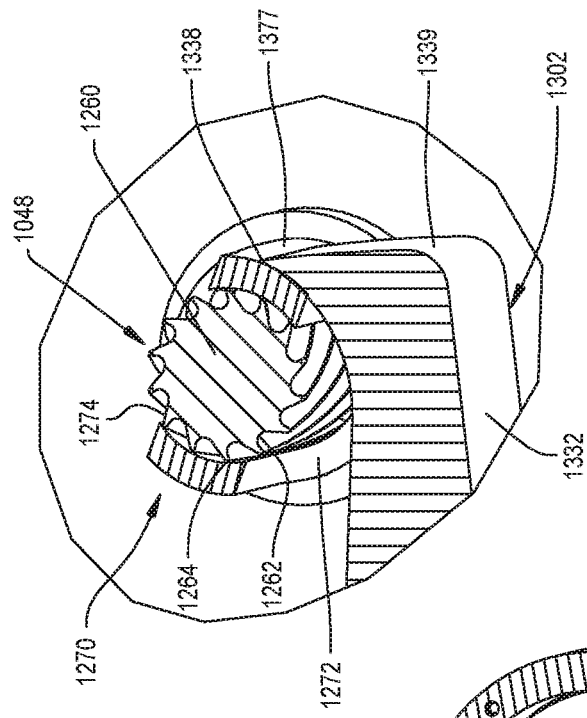
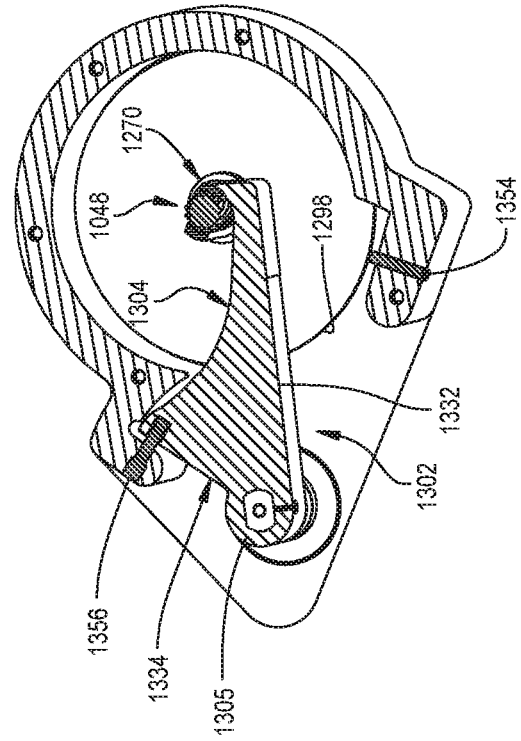
FIG. 35
FIG. 34

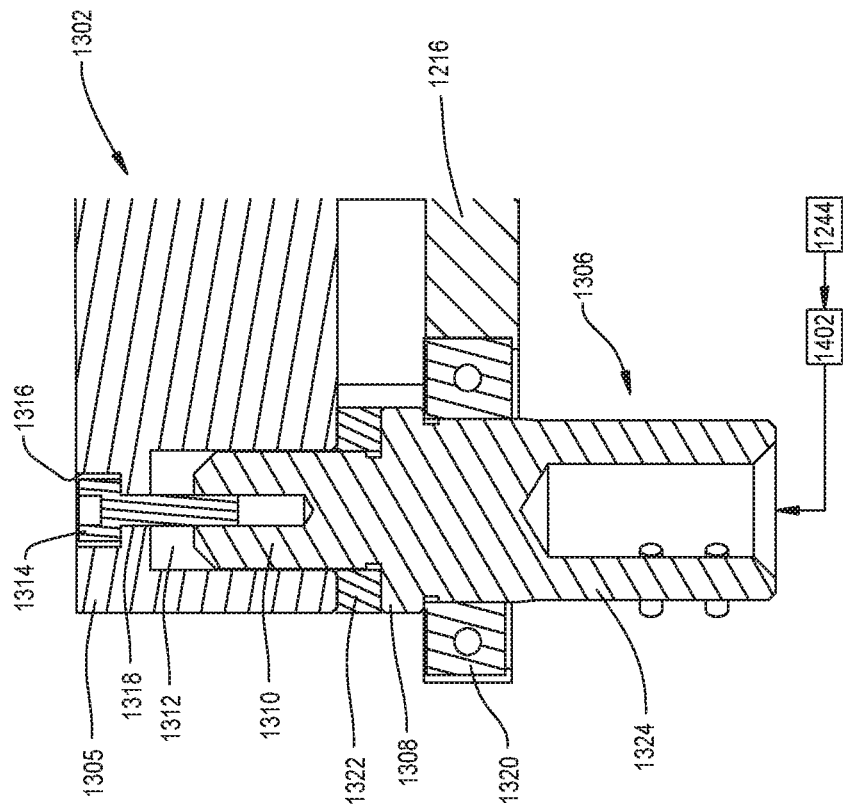

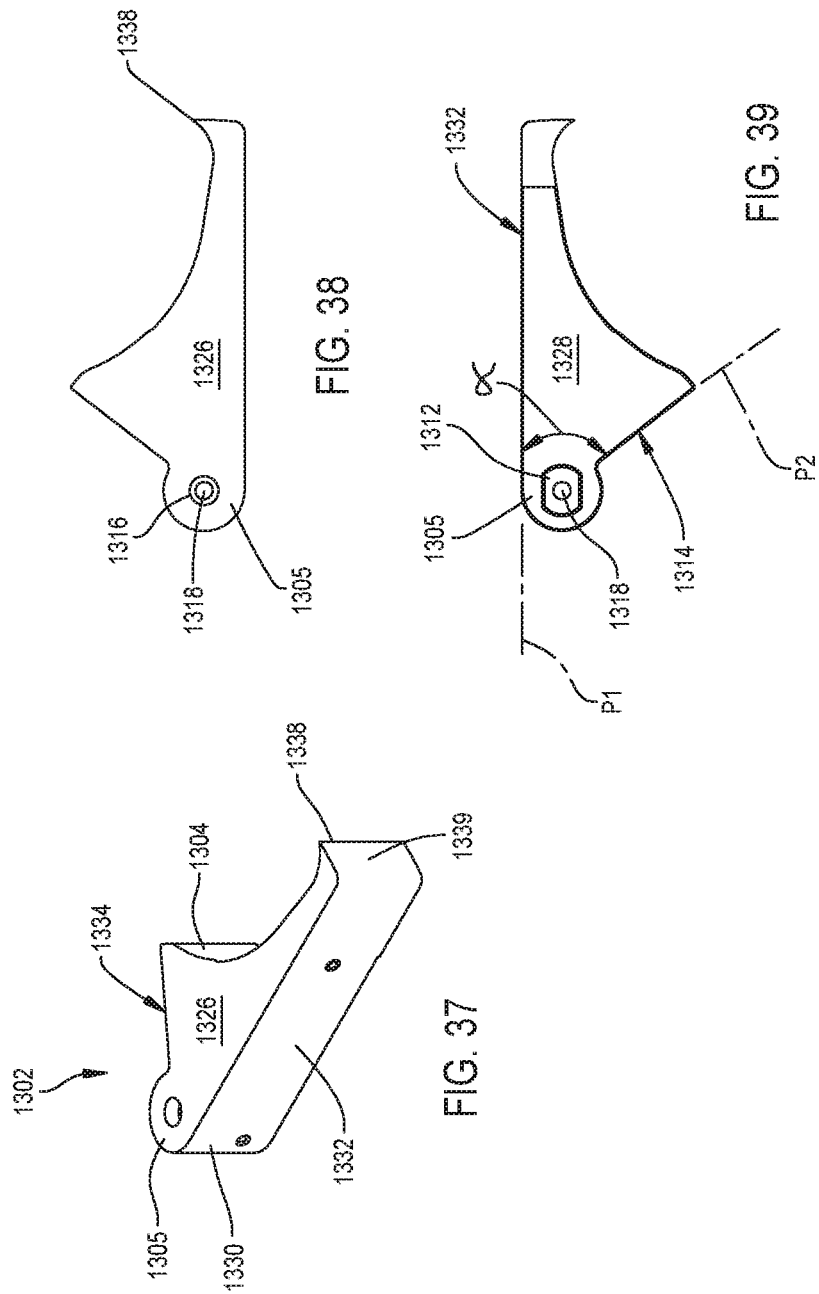

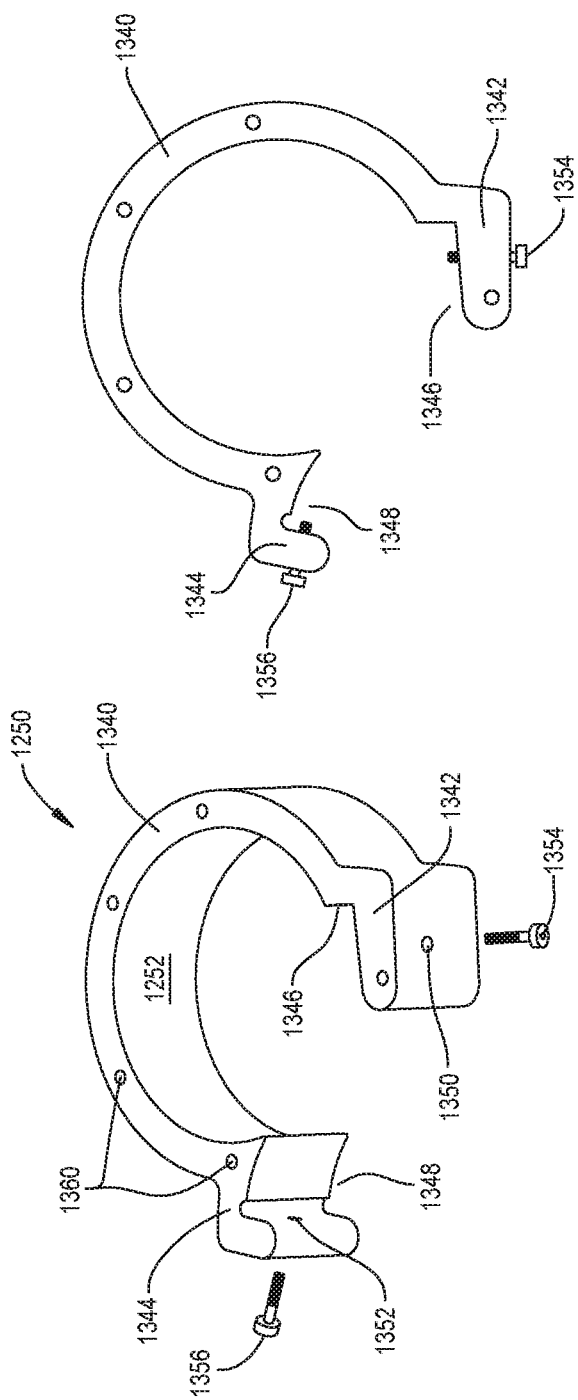

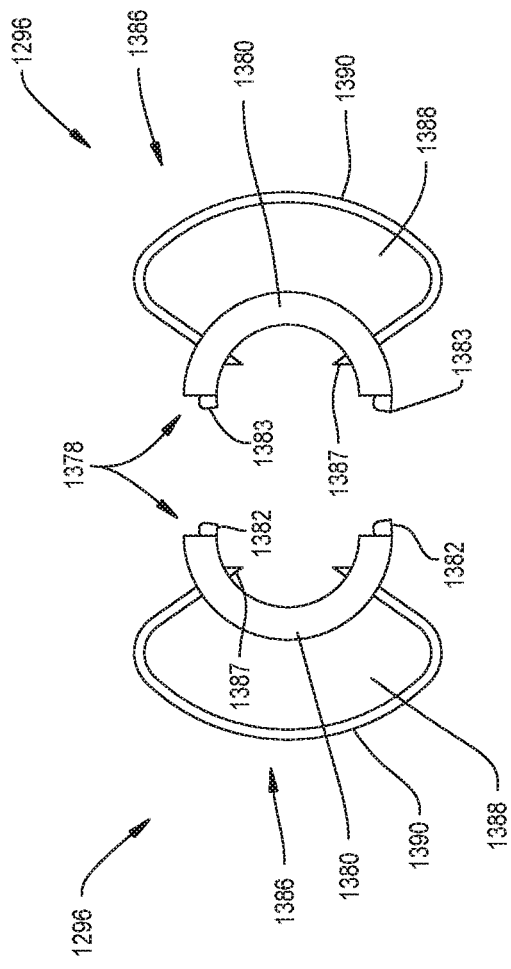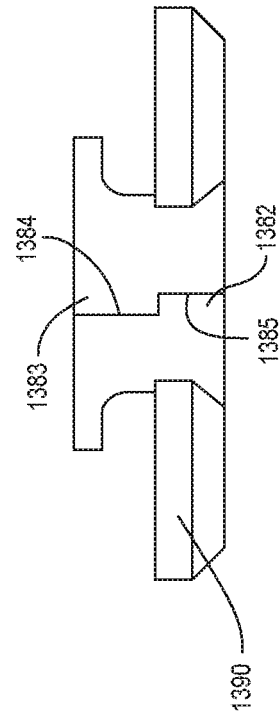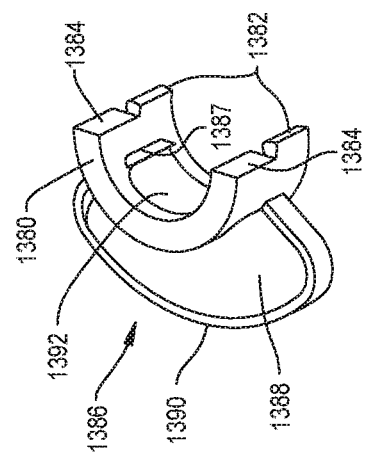

BONE CLEANING ASSEMBLY

RELATIONSHIP TO EARLIER FILED APPLICATIONS

This application is a continuation of U.S. patent application Ser. No. 16/018,660 filed 26 Jun. 2018. U.S. patent application Ser. No. 16/018,660 is a continuation of U.S. patent application Ser. No. 15/627,488 filed 20 Jun. 2017 now U.S. Pat. No. 10,034,673. U.S. patent application Ser. No. 15/627,488 is a divisional of U.S. patent application Ser. No. 14/311,674 filed 23 Jun. 2014 now U.S. Pat. No. 9,687,361. U.S. patent application Ser. No. 14/311,674 is a continuation of PCT Pat. App. No. PCT/US2012/072160 filed 28 Dec. 2012. PCT App. No. PCT/US2012/072160 is a non-provisional application that claims priority from U.S. Prov. Pat. App. No. 61/581,310 filed 29 Dec. 2011. The contents of the above-identified applications from which this application claims priority are incorporated herein by reference.

FIELD OF THE INVENTION

This invention relates to an assembly able to clean bone stock for use in surgical procedures.

BACKGROUND OF THE INVENTION

In certain surgical procedures chip-sized bone is used as filler adjacent intact bone. For example, in a spinal fusion procedure, it is known to place a compound formed out of milled bone chips around implanted rods. The rods hold adjacent vertebrae in alignment. This compound serves as a lattice upon which tissues forming the vertebrae grow so as to form a foundation of bone around the rods. This foundation distributes the load imposed on the rods. Bone chips can also be placed in the intervertebral disc space or into a cage positioned in the intervertebral disc space.

Bone chips are also used as filler and/or growth formation lattice in orthopedic surgical procedures and maxillofacial procedures. Bone chips are used as a filler and/or growth formation lattice in these procedures because the proteins from which the bone is formed serve as make-up material from which the blast cells of the adjacent living bone cells form new bone.

The ideal source of bone stock for bone chips is the patient into whom the bone chips are to be packed. This is because the patient's own bone is less likely than donor bone to be rejected by the patient's immune system. Accordingly, in a procedure in which bone chips are required, bone stock is often harvested from one of the patient's bones that can afford to lose a small section of bone, typically between 0.25 and 3 cubic centimeters. Bone that is removed from the patient for transplant into another part of the patient is referred to as autograft bone.

Converting autograft bone stock into bone chips can generally be considered a two part process. In the first part of the process, the harvested bone is cleaned to remove the ligaments and other soft tissue that is not suitable for forming bone chips. The cleaned bone is then milled into bone chips. The Applicant's Assignee's U.S. Patent Application Pub. No. US 2009/0118735 A1 and PCT Pub. No. WO 2009/061728 A1, BONE MILL INCLUDING A BASE AND A MILL HEAD SEPARATE FROM THE BASE, THE MILL HEAD INCLUDING A REMOVABLE CATCH TRAY, the contents of which are hereby incorporated by reference, discloses an electrically operated bone mill capable of converting bone stock into bone chips.

In a typical bone cleaning process, prior to milling the bone, surgical personnel manually clean the bone. Presently, surgical personnel perform this manual process using curettes and/or rongeurs. It may take 15 minutes or more for surgical personnel to perform this task.

Moreover, to perform the cleaning process, the surgical personnel may need to firmly grasp the bone. Exerting such force on the bone may cause tearing of the gloves worn by the surgical personnel. Furthermore, the sharp cutting tools being used by the surgical personnel could cut or tear through the gloves. Such cutting or tearing through the gloves could result in the possibility that skin of the surgical personnel may come into direct contact with the bone. This contact can result in contamination of the bone.

Therefore, there is a need in the art for assemblies that remove soft tissue from bone while reducing the need for manual grasping and cleaning of the bone.

SUMMARY OF THE INVENTION

This invention provides an assembly for cleaning bone stock. The assembly comprises a shell defining a void space for receiving the bone stock to be cleaned. A cutter is disposed in the void space so that, when actuated, the cutter cleans the bone stock by removing soft tissue from the bone stock. A guide moves between a disengaged position and an engaged position. The guide is configured to, when out of the disengaged position, move bone stock received in the void space toward the cutter.

This invention also provides another assembly for cleaning bone stock. This assembly includes a shell defining a void space for receiving the bone stock to be cleaned. A cutter is disposed in the void space so that, when actuated, the cutter cleans the bone stock by removing soft tissue from the bone stock. A shaving tube is coaxially disposed about the cutter and is supported by the shell. The cutter and the shaving tube are configured to rotate at different speeds or directions relative to one another.

BRIEF DESCRIPTION OF THE SEVERAL VIEWS OF THE DRAWINGS

Advantages of the invention will be readily appreciated as the same becomes better understood by reference to the following detailed description when considered in connection with the accompanying drawings wherein:

FIG. 11A is a close-up of FIG. 10 illustrating interaction between the cutter, shaving tube, bone stock, and guide with a horizontal cross-section taken through the cutter and shaving tube;

FIG. 14 is a top perspective view of the cutter;

FIG. 15 is an elevational view of the cutter;

FIG. 16 is a close-up of a flute and cutting edge of the cutter of FIGS. 14 and 15 viewed from below the cutter;

FIGS. 14A-16A are views similar to the views of FIGS. 14-16 of an alternative cutter;

FIGS. 14B-16B are views similar to the views of FIGS. 14-16 of a second alternative cutter;

FIG. 22 is an exploded perspective view of the cleaning module and drive module without their shells;

FIG. 23A is a partial perspective view showing a lower portion of a hub of the guide and a cam follower;

FIGS. 23B-23E are schematic illustrations of movement of the cam follower and corresponding movement of the guide with FIG. 23B showing the guide in an extreme clockwise position, FIG. 23C showing the guide momentarily in the extreme clockwise position, FIG. 23D showing the guide in the extreme counterclockwise position, and FIG. 23E showing the guide in an engaged position with bone stock trapped between the guide and cutter;

FIG. 23F is a cross-sectional view taken through the hub of guide and the cam follower;

FIG. 24 is a top view of a cam gear;

FIG. 34 is an upper cross-sectional perspective view of the arm and the containment ring of the alternative cleaning module;

FIG. 35 is an enlarged, fragmentary view of FIG. 34 illustrating engagement of the arm and a shaving tube of the alternative cleaning module;

FIG. 36 is a partial cross-sectional view of the alternative cleaning module;

FIG. 37 is a perspective view of an arm of the alternative cleaning module;

FIG. 38 is a top view of the arm of the alternative cleaning module;

FIG. 39 is a bottom view of the arm of the alternative cleaning module;

FIG. 40 is a perspective view of a containment ring of the alternative cleaning module;

FIG. 41 is a top view of the containment ring of the alternative cleaning module;

FIG. 48 is a top view of a pair of debris catches of the alternative cleaning module;

FIG. 49 is a perspective view of one of the debris catches of FIG. 48; and

FIG. 50 is a side view of the debris catches of FIG. 48 mated together.

DETAILED DESCRIPTION

I. Assembly

Figure 1:
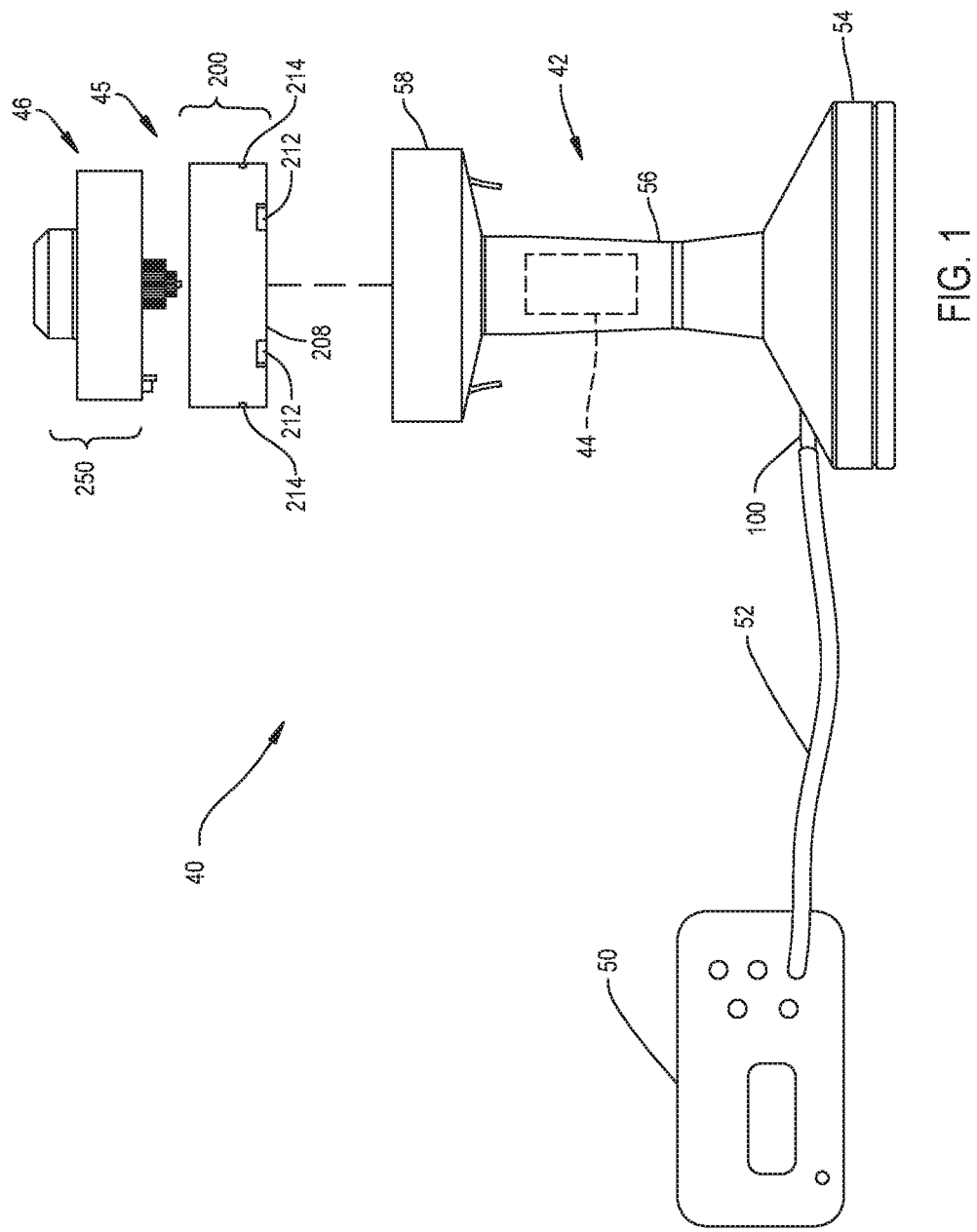
FIG. 1 is an elevational view of a system for cleaning bone stock including a base unit, a cleaning module, a drive module, and a console.

Referring to the Figures, a bone cleaning system for cleaning bone stock is generally shown at 40 in FIG. 1.

System 40 includes a base unit 42. Internal to the base unit 42 is a drive motor 44. A drive module 45 is configured to be removably attachable to the base unit 42 for coupling to the motor 44. A cleaning module 46, for cleaning bone stock, is removably attachable to the drive module 45. In the embodiment shown, the base unit 42 and drive module 45 are reusable, while the cleaning module 46 is disposable for discarding after the bone stock is cleaned.

Figure 4:
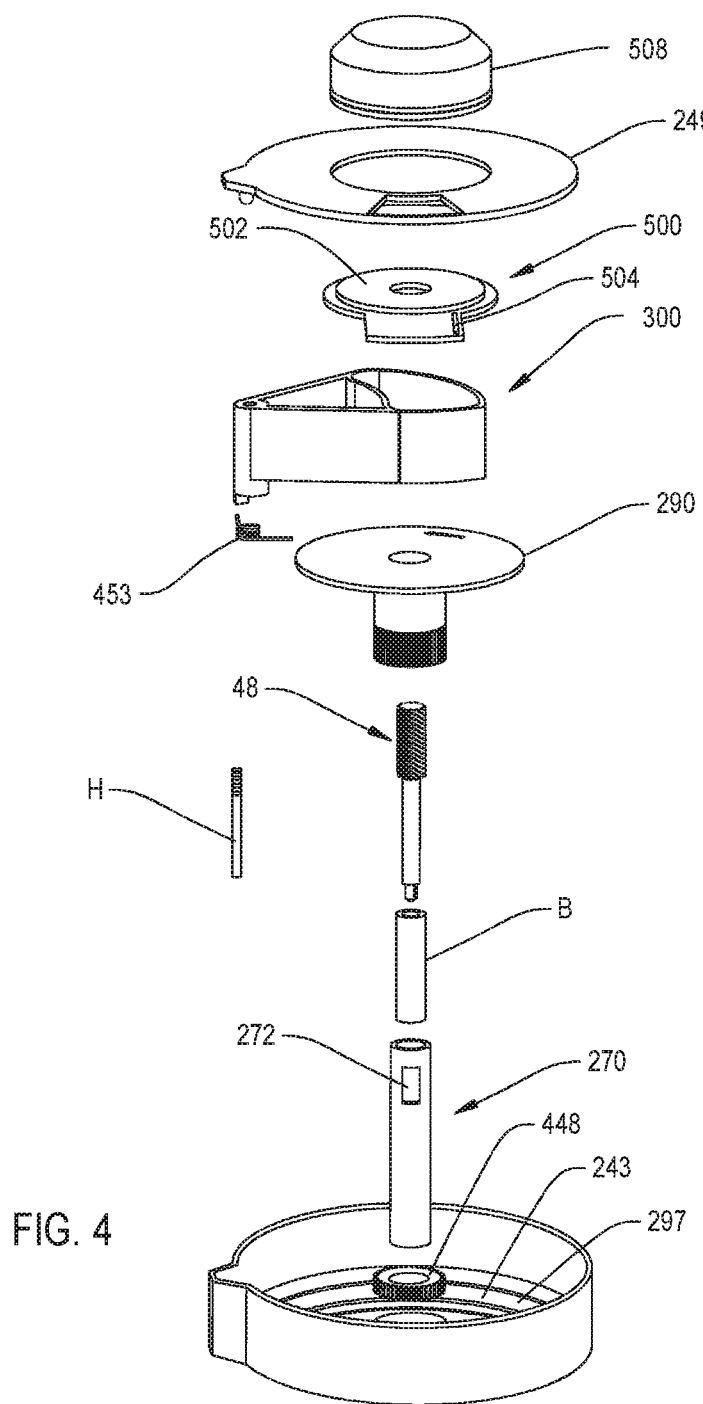
FIG. 4 is an exploded perspective view of the cleaning module.
Figure 7:
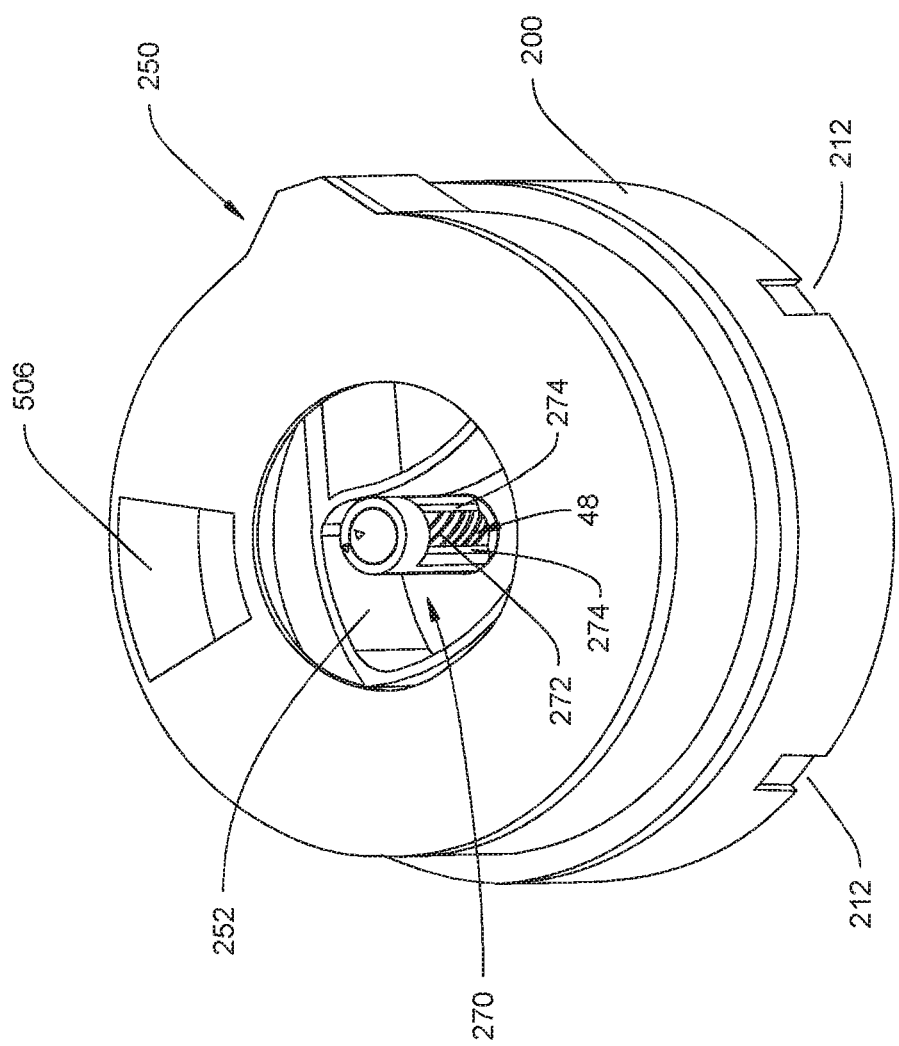
FIG. 7 is a perspective view of the cleaning module with a cap and lid removed.

The cleaning module 46 includes at least one cutter 48 for cutting soft tissue from bone stock (see FIGS. 4 and 7). Cleaning module 46 is configured so that, when attached to the drive module 45 positioned on base unit 42, cutter 48 is operatively connected to the motor 44 though the drive module 45 so as to be actuated by the motor 44.

Harvested bone stock is placed in the cleaning module 46. The motor 44 is actuated so as to result in an actuation of the cutter 48. The action of the cutter 48 cuts the soft tissue and other debris from the bone stock while leaving a progenitor layer around the bone in place.

A control console 50 supplies electrical energization signals to the motor 44 to actuate the motor 44. Cable 52 is connected between the base unit 42 and console 50. Cable 52 contains the conductors (not illustrated) over which the energization signals are supplied from the console 50 to the motor 44.

The base unit 42 includes a circular foot 54. A leg 56 extends upwardly from foot 54. Leg 56 is tubular in shape and has a circular cross section. A pedestal 58 is disposed on top of the leg 56. The pedestal 58 tapers radially outwardly from the leg 56.

Figure 2:
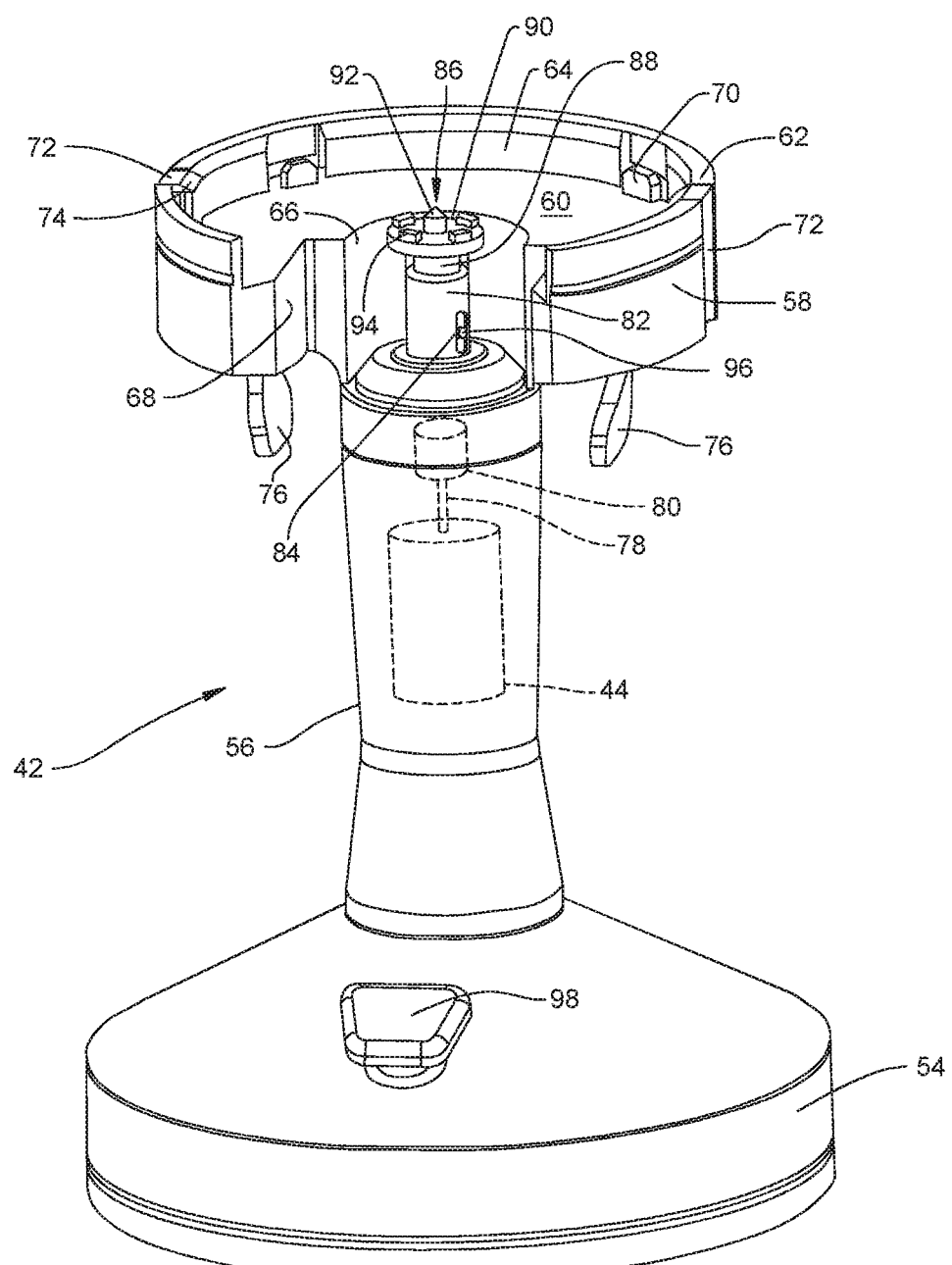
FIG. 2 is a perspective view of the base unit of FIG. 1.
Figure 3:
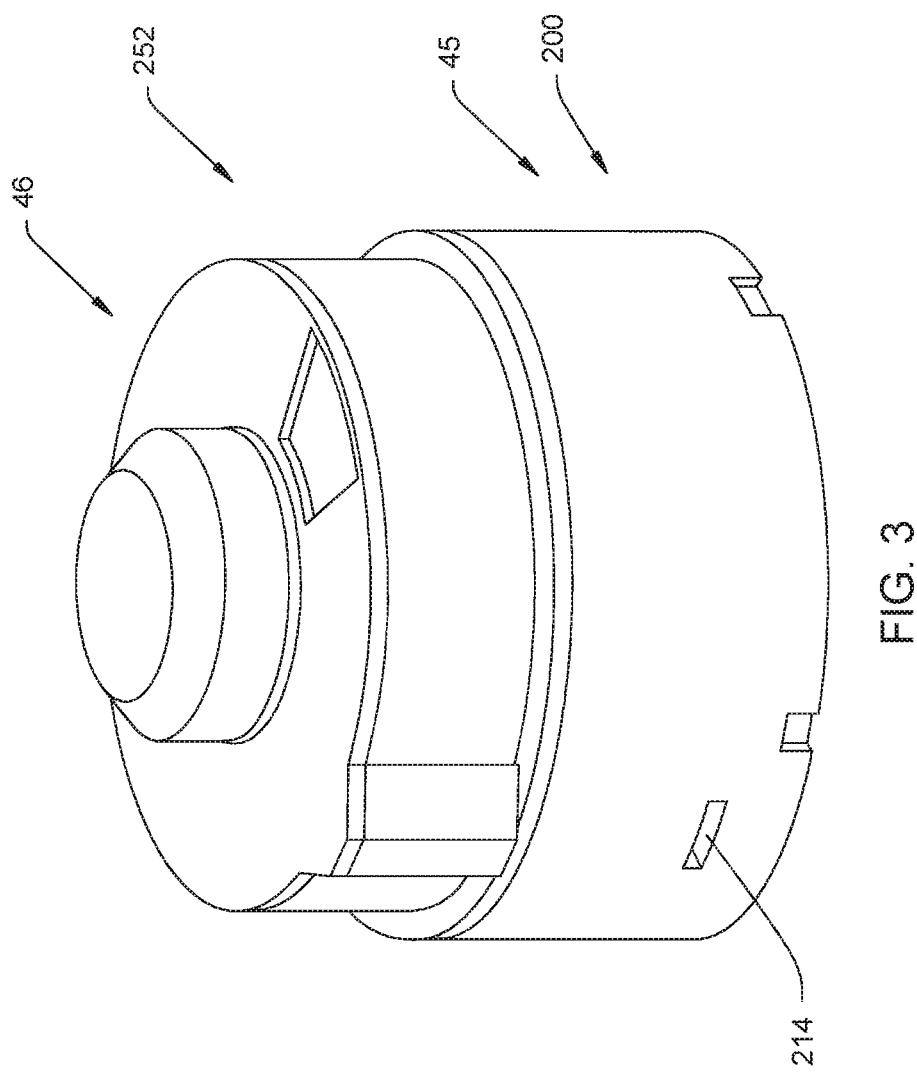
FIG. 3 is a perspective view of the cleaning module and drive module.

Referring to FIG. 2, pedestal 58 has a generally circular top surface 60. The pedestal is further formed to have a lip 62 that extends upwardly and extends about the perimeter of the top surface 60. Top surface 60 and the radially inner surface of lip 62 define a substantially cylindrical mounting space 64 within pedestal 58. Mounting space 64 is open at the top of the pedestal 58. The outer circumference of lip 62, which is the outer circumference of the pedestal 58, is smaller than a circumference of the foot 54. The outer circumference of lip 62 is larger than that of leg 56. Pedestal 58 is further formed so as to have an opening 66 in the center of top surface 60.

Notch 68 extends radially inwardly from the outer circumference of pedestal 58. Notch 68 thus forms a break in lip 62. In the illustrated version of the invention notch 68 extends radially inwardly to center opening 66. The pedestal 58 further includes a number of circumferentially and equi-angularly spaced apart teeth 70 (only two teeth shown in FIG. 2). Each tooth 70 extends upwardly from the pedestal top surface 60 adjacent lip 62.

Two retention arms 72 are pivotally mounted to the pedestal 58. Retention arms 72 are diametrically opposed and mounted to the pedestal 58 in cutouts formed in the lip 62 (cutouts not separately numbered).

Each retention arm 72 has a finger 74 that, when the arm 72 is at rest, extends over a portion of the perimeter of pedestal top surface 60. When the retention arms 72 are so positioned, the arms 72 are in the "locked" state.

Each retention arm 72 has a lever 76 located below the pedestal 58. By moving lever 76 radially inwardly, towards the underside of the pedestal 58, the associated retention arm 72 is pivoted relative to the pedestal 58 so as to move the corresponding finger 74 away from its position over the pedestal top surface 60 and out of its locked state. When the retention arms 72 are so positioned, the arms 72 are in the "released" state.

A biasing device such as a spring (not illustrated) is disposed between an inner surface of the pedestal 58 and each arm 72. The spring biases its respective retention arm 72 towards its locked state. Each retention arm 72 may be biased into its locked state by a dedicated spring. Alternatively, both retention arms 72 may be biased into their locked states by a common, shared spring.

Motor 44 includes a rotatable output shaft 78 disposed in a central hollow of leg 56. Output shaft 78 extends from motor 44 upwardly toward pedestal center opening 66. A gear fixed to the top of output shaft 78 (gear not illustrated) engages a gear train 80 disposed in leg 56 above the motor 44. Gear train 80 steps down the rotational speed of the motor output shaft 78.

The gear train 80 has a rotatable output drive shaft 82 extending from the top of leg 56. Drive shaft 82 is disposed in the pedestal center opening 66 below the top surface 60. Drive shaft 82 is tubular in shape. Drive shaft 82 is provided with two diametrically opposed slots 84 (one shown in FIG. 2) that extend longitudinally between opposite, closed ends along drive shaft 82. Slots 84 each extend radially through the cylindrical wall of tubular drive shaft 82. Each slot 84 has a parallel pair of elongate interfacing sides extending between its closed, opposite slot ends.

In some versions of the invention, motor 44 and gear train 80 are collectively provided so that the gear train drive shaft 82 can rotate at speeds between 100 and 500 RPM. These speeds are the under load speeds at which the drive shaft 82 rotates during operation of the bone cleaning system 40 when bone stock is disposed in the cleaning module 46. Motor output shaft 78, gear train 80, and drive shaft 82 are described in greater detail in US Pat. Pub. No. 2012/0310243 A1, hereby incorporated by reference herein.

A drive spindle 86 is coupled to and driven by drive shaft 82. The drive spindle 86 includes a cylindrical stem 88. At the upper axial end of stem 88, spindle 86 has a concentric, disc shaped head 90. Spindle head 90 is circular, and may be affixed to stem 88. Alternatively, spindle head 90 may be integrally formed with stem 88.

A number of features extend upwardly from the planar top surface of the spindle head 90. One of these features is an alignment pin 92. The alignment pin 92 is coaxial with the longitudinal axis of the spindle 86 and projects upwardly from the center of the head 90. Pin 92 is cylindrical adjacent the planar top surface of the spindle head 90. Alignment pin 92 may be formed on the axial end of stem 88 and project through the center of spindle head 90. Alternatively, alignment pin 92 and spindle head 90 may both be integrally formed with stem 88. Alternatively, alignment pin 92 and spindle head 90 may be integrally formed and affixed to the axial end of stem 88. The terminal end of alignment pin 92 is frustoconical and provided with a flattened tip. These features of alignment pin 92 are not separately numbered.

Four circumferentially and equiangularly spaced apart drive teeth 94 also extend upwardly from the planar top surface of the spindle head 90. Drive teeth 94 are distributed about the perimeter of the spindle head 90. Drive teeth 94 have arcuate, radially outer surfaces that are flush with the radially outer circular edge of the spindle head 90. Drive teeth 94 also have arcuate, radially inner surfaces. Extending between the radially outer and inner surfaces of each drive tooth 94 is a pair of circumferentially opposite, inwardly tapered side surfaces; these surfaces of drive teeth 94 are planar and perpendicular to the planar top surface of the spindle head 90, and are not separately numbered. Drive teeth 94 do not extend as far as alignment pin 92 does from the planar top surface of spindle head 90.

Spindle 86 is dimensioned and positioned so that cylindrical stem 88 is slidably received in the coaxial, longitudinal bore of the tubular drive shaft 82. A cylindrical drive pin 96 is fitted into a cross bore (not separately numbered) extending radially through the spindle stem 88. The opposed ends of the drive pin 96 extend from the cylindrical surface of stem 88, and are disposed in the diametrically opposed slots 84 formed in tubular drive shaft 82. Near its opposite ends, drive pin 96 abuts and slidably engages the circumferentially interfacing elongate sides of the slots 84. There is little or no relative angular movement between the tubular drive shaft 82 and the coaxial stem 88. Rotation of the drive shaft 82, induced by motor 44 through the gear train 80, is imparted to the stem 88 through the abutting engagement between drive pin 96 and the sides of slots 84.

Stem 88 and tubular drive shaft 82 have relative coaxial movement in a range limited by the length of slots 84. In this range, and relative to leg 56, stem 88 thus has an uppermost axial position which is limited by abutting engagement between drive pin 96 and the top ends of slots 84, and a lowermost axial position which is limited by abutting engagement between drive pin 96 and the bottom ends of slots 84. The engagement between slots 84 and drive pin 96 retains the drive spindle 86 to the drive shaft 82 and transfers torque therebetween. Hence, the drive spindle 86 rotates in unison with the drive shaft 82 and is able to move longitudinally relative to the gear train 80.

A push-button switch 98 is mounted to the base unit foot 54. The push button of switch 98 is biased with a spring (not illustrated) into its extended position, in which switch 98 is electrically open. Depression of the push button against this spring-biased force electrically closes switch 98. A socket 100, shown in FIG. 1, receives cable 52 from control console 50 and includes terminals that are electrically connected to the cable conductors.

Internal to foot 54 is a circuit board (not illustrated) electrically in series between socket 100 and motor 44. Mounted to the circuit board are electrical components that function as an electric motor controller. The function of the motor controller is to regulate power received at socket 100 for energizing motor 44. Switch 98 is placed electrically in series between socket 100 and the circuit board. Alternatively, switch 98 is placed electrically in series between the circuit board and motor 44. Power received from console 50 through cable 52 and socket 100 is regulated by the motor controller and provided to the windings of motor 44 when switch 98 is electrically closed. Power to the motor 44 is discontinued when the push button is released and switch 98 electrically opens. The specific structure and configuration of these electrical components are of any suitable type well known to those of ordinary skill in the motor control-related arts and are not illustrated.

Drive module 45 includes a shell 200. Shell 200 is dimensioned to fit to the base unit 42 so that the base unit motor 44, when actuated, drives a gear train 201 (see FIG. 5) in the drive module 45 that ultimately drives the cutter 48 and other components in the cleaning module 46 to clean bone stock.

Shell 200 has a bottom 208 and an outer wall 204. Outer wall 204 has an outer periphery that allows the shell 200 to be slip fitted into the mounting space 64 above pedestal top surface 60 and within lip 62.

Four circumferentially and equiangularly spaced apart notches 212 extend radially inward in, and axially upward from, a downwardly directed face of the outer wall 204 (two notches are shown in FIG. 1). Notches 212 are dimensioned so that when the shell 200 is fitted to base unit 42, pedestal teeth 70 are seated in the notches 212. Engagement of the teeth 70 and notches 212 prevents unwanted rotation of the shell 200 relative to the base unit 42 during operation.

Outer wall 204 is further provided with two additional side notches 214 that are diametrically opposed from each other. Side notches 214 extend radially inwardly from an outer cylindrical surface of the outer wall 204 at a location above a bottom of the outer wall 204. More particularly, shell 200 is formed so that when the shell 200 is seated in pedestal mounting space 64 and teeth 70 are seated in notches 212, side notches 214 are positioned to receive the radially inwardly directed fingers 74 of retention arms 72.

The fingers 74 are biased radially inwardly to seat against cooperating surfaces of the side notches 214 to selectively lock shell 200 to base unit 42. The upper surfaces of fingers 74 may be downwardly angled radially inwardly. This allows shell 200 to slidably engage and move fingers 74 radially outward against the biasing force acting on retention arms 72. Thus, shell 200 may be pushed downwardly past the fingers 74 and received in mounting space 64 without levers 76 being manually actuated.

Shell 200 further includes a base plate 215 and a top 216. Top 216 is fixed to the outer wall 204 by fasteners, ultrasonic welding, or adhesive (not illustrated). Base plate 215 is integral with the outer wall 204. Outer wall 204 extends upwardly from base plate 215 to define a lower cavity 218 of shell 200. The gear train 201 is secured to the shell 200 within the lower cavity 218.

Figure 5:
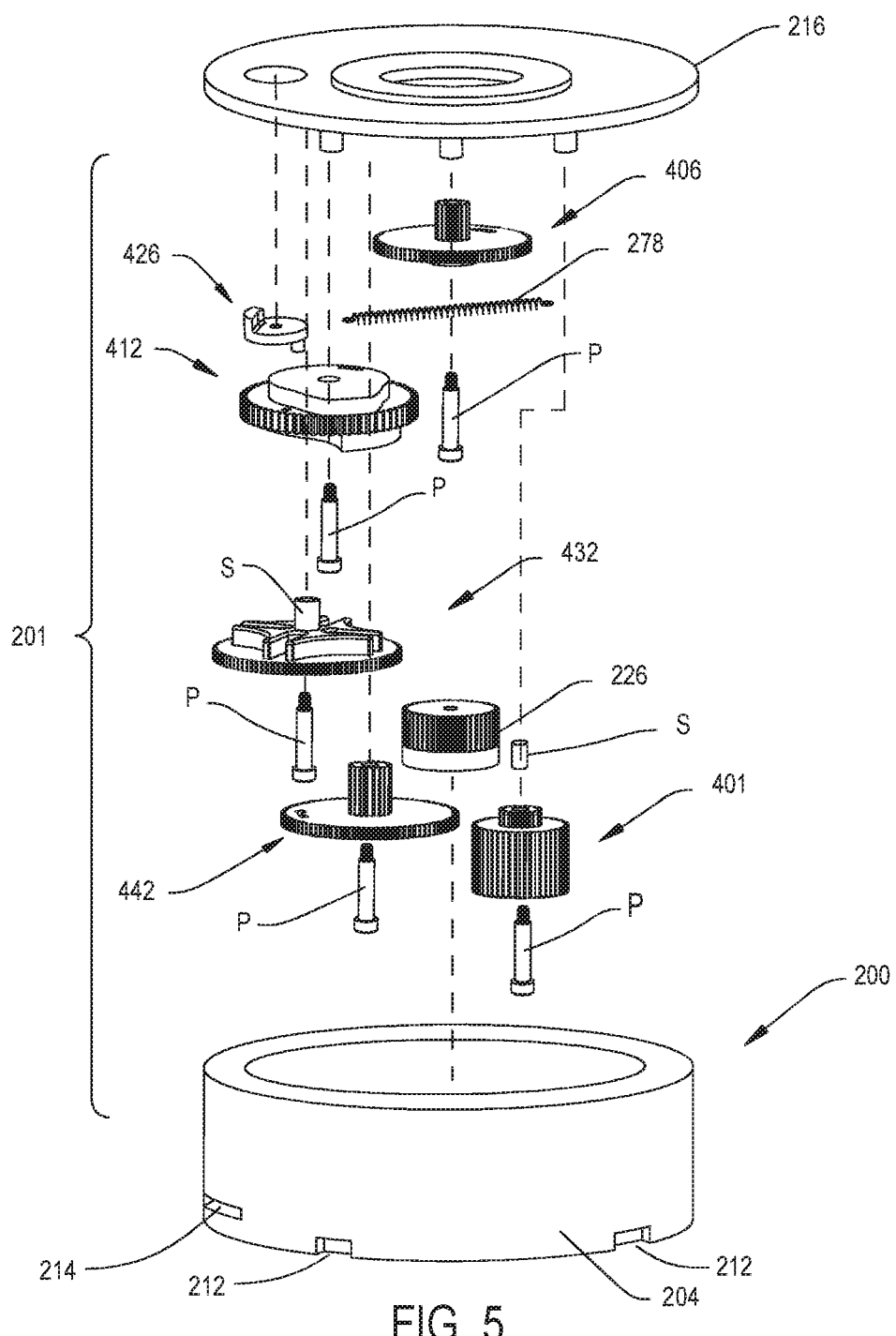
FIG. 5 is an exploded perspective view of the drive module.
Figure 6:
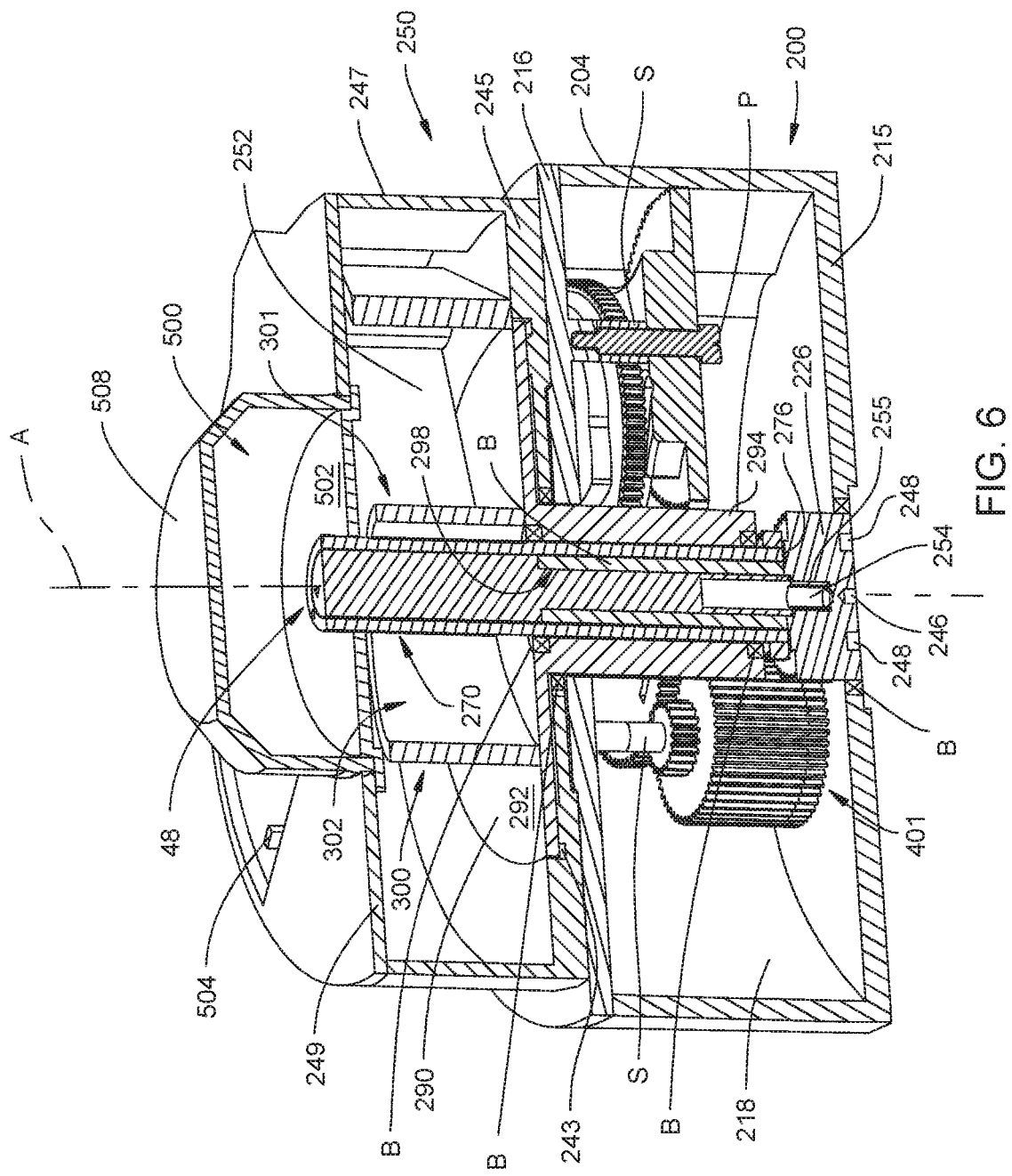
FIG. 6 is a cross-sectional view of the cleaning module and drive module.

A drive gear 226, shown in FIGS. 5 and 6, is supported to rotate within the shell 200. In particular, a lower portion of the drive gear 226 is cylindrical and smooth and is rotatably supported by a bearing member B in the base plate 215 of shell 200. An upper portion of the drive gear 226 is a spur gear that is cylindrical in shape. When shell 200 is received in mounting space 64 of pedestal 58, drive gear 226 engages the spindle head 90. Driving torque is transferred from the spindle head 90 to the drive gear 226.

Drive gear 226 has a downwardly directed face with recesses having corresponding shapes and locations that cooperate with those of the alignment pin 92 and the drive teeth 94 protruding upwardly from the top surface of the spindle head 90. More particularly, drive gear 226 includes a centrally located alignment pin recess 246 and four circumferentially and equiangularly spaced apart drive tooth-receiving recesses 248. Recesses 246 and 248 receive alignment pin 92 and drive teeth 94, respectively. The walls of each drive tooth recess 248 are parallel to the respectively interfacing surfaces of the drive tooth 94 slidably received therein. Spindle head 90 and drive gear 226 thus define a dog clutch for transferring torque from the spindle head 90 to the drive gear 226 when shell 200 is received in mounting space 64 of pedestal 58, and teeth 94 and recesses 248 are mated.

The cleaning module 46 also has a cleaning module shell 250. Cleaning module shell 250 includes a cleaning module base 245. Cleaning module base 245 has a recess (not numbered) shaped to seat on a boss (not numbered) located on the top 216 of the shell 200 of drive module 45. An outer peripheral wall 247 is integral with the cleaning module base 245 and extends upwardly from the cleaning module base 245. A top 249 is fixed about its periphery to the outer peripheral wall 247 by fasteners, ultrasonic welding, or adhesive (not illustrated).

As shown in FIG. 7, cleaning module shell 250 defines a void space 252 for receiving harvested and uncleaned bone stock. During use, cutter 48 cleans the bone stock in the void space 252 by cutting soft tissue and other debris from the bone stock.

Cutter 48 is located within void space 252. The cutter 48 is supported to rotate about central axis A. The cutter 48 includes a shaving rotor 260 with helical flutes 262 having cutting edges 264 (not shown for simplicity in FIG. 6, but see FIGS. 14-16). During operation of system 40, cutter 48 rotates about central axis A and the cutting edges 264 clean bone stock in the void space 252 by cutting soft tissue from the bone stock. Cutter 48 rotates in a counterclockwise direction about central axis A (as viewed from above).

A shaving tube 270 extends coaxially about the cutter 48, as shown in FIGS. 6 and 7. Shaving tube 270 defines a cutter window 272 through which tissue attached to the bone stock is received for engagement by the cutter 48. The cutter window 272 is bounded by two shaver edges 274. The shaver edges 274 are sharp so as to cut soft tissue caught between the shaving rotor 260 of cutter 48 and the shaving tube 270 when the shaving rotor 260 rotates relative to the shaving tube 270. The shaver edges 274 also act as impingement structures against which soft tissue abuts and is temporarily held to facilitate cutting by shaving rotor 260 of cutter 48.

Shaving tube 270 is configured to make one complete rotation (approximately 360 degrees) about central axis once every 1 to 10 seconds in a counterclockwise direction, or in some case, once every 1 to 5 seconds. Complete rotation of the shaving tube 270 alternates with periods of time in which the shaving tube 270 is stationary and not rotating. When rotating, shaving tube 270 rotates at about 30 to 120 RPM.

Owing to the helical geometry of flutes 262, and the relatively slow rotation of shaving tube 270 compared to cutter 48, as the cutter 48 rotates, cut soft tissue is augered axially upwardly along cutter 48 between the cutter 48 and the shaving tube 270 to be expelled out of a top end of the shaving tube 270 (see FIG. 6). In essence, the cutter 48 acts as a screw conveyor. The space between the cutter 48 and the shaving tube 270 is a debris passage through which the cut soft tissue is augered and ultimately expelled.

A lid 500 (removed in FIG. 7, but shown in FIGS. 4 and 6) is rotatably disposed about the shaving tube 270 near the top end. The lid 500 defines a collecting surface 502 onto which the tissue that exits from the top end of the shaving tube 270 can fall. The collecting surface 502 is spaced below the top end of the shaving tube 270 to act as a debris catch.

The lid 500 has a slide handle 504. Handle 504 extends upwardly from the lid 500 to be grasped by the user. The user can slide the lid 500 to uncover an opening 506 in the cleaning module shell 250 through which the bone stock can be received to place the bone stock in the void space 252.

A cap 508 is attached to the cleaning module shell 250 to cover and enclose the collecting surface 502. The cap 508 defines a collecting space into which the cut soft tissue is stored for later retrieval or disposal.

Figure 8:
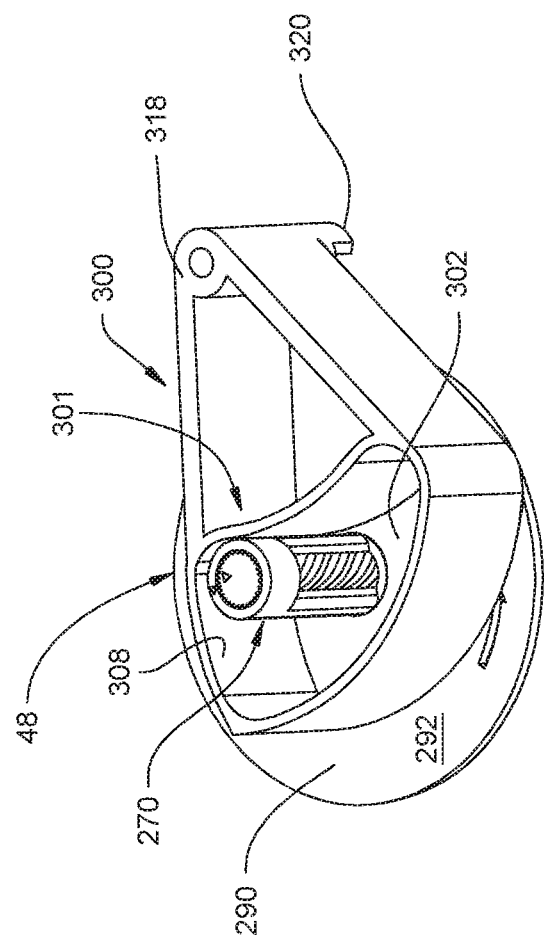
FIGS. 8 and 9 are top perspective views of a cutter, guide, shaving tube, and tumble plate.
Figure 9:
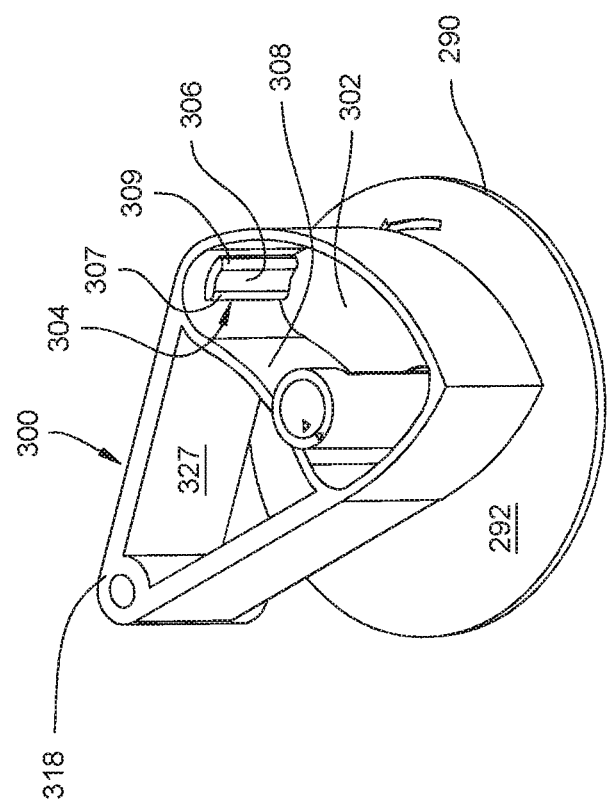
Figure 10:
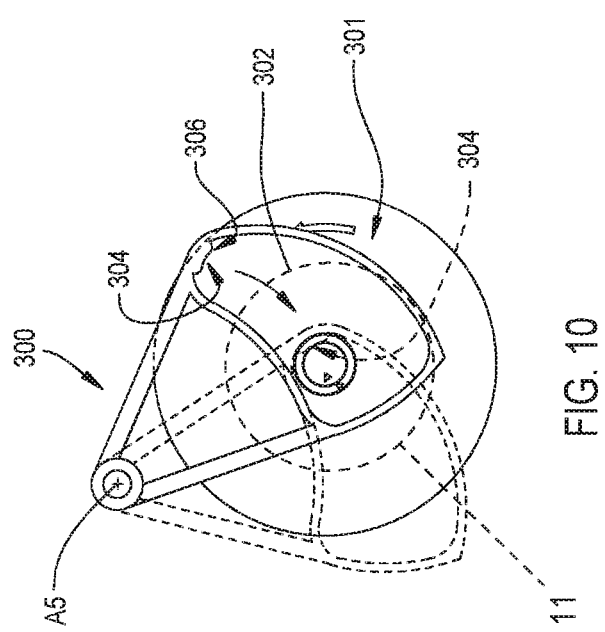
FIG. 10 is a top view of the cutter, guide, shaving tube, and tumble plate illustrating different positions.

Referring to FIGS. 8-10, which show the cleaning module 46 with shell 250, lid 500, and cap 508 removed, a circular tumble plate 290 is operatively coupled to the cutter 48 to rotate with the cutter 48 at the same speed. The bone stock sits on top of the tumble plate 290 during cleaning so that, when actuated, the tumble plate 290 carries the bone stock to reorient the bone stock relative to the cutter 48 for more efficient cutting of the soft tissue from the bone stock. During operation of system 40, tumble plate 290 is driven to rotate about central axis A.

An upper surface 292 of the tumble plate 290 carries the bone stock. In the embodiment shown, the upper surface 292 is flat and smooth. In some embodiments, the upper surface 292 is textured or has gripping features (not illustrated) to grip the bone stock and facilitate moving the bone stock.

A tubular shaft 294 is fixed to the tumble plate 290, as shown in FIG. 6. Tubular shaft 294 extends downwardly from the tumble plate 290. The tubular shaft 294 is coaxially disposed about the shaving tube 270. Bearing members B are located between the tubular shaft 294 and the shaving tube 270 to facilitate smooth relative rotation between the tubular shaft 294 and the tumble plate 290. Likewise, a bearing member B is located between tubular shaft 294 and cleaning module base 245. As will be described further below, the tumble plate 290 is constantly rotating, while the shaving tube 270 periodically rotates. Bearing members B are shown schematically and may include bearings, bushings, or the like.

Tumble plate 290 is disposed in a recess 243 in a top surface (not numbered) of the cleaning module base 245 (see FIG. 6). A lower surface (not numbered) of the tumble plate 290 rides on a raised ring-shaped section 297 of cleaning module base 245. The ring-shaped section 297 (see FIG. 4) is disposed in the recess 243. Upper surface 292 of tumble plate 290 is coplanar with the top surface of the cleaning module base 245. In some embodiments, the upper surface 292 of tumble plate 290 is slightly recesses below top surface of the cleaning module base 245. Ring-shaped section 297 is formed of low friction material to facilitate rotation of the tumble plate 290 thereon. Alternatively, the tumble plate 290 rides on bearing members (not illustrated) in the recess 243.

An arm 300 extends over the planar upper surface 292 of tumble plate 290. The arm 300 may be spaced above the upper surface 292 of tumble plate 290 to provide a small gap therebetween. The gap can be sized to prevent bone stock from passing therethrough. In other embodiments, the arm 300 rides on the upper surface 292 of tumble plate 290. The arm 300 acts as a guide to direct and press the bone stock into the cutter 48 through the cutter window 272 of the shaving tube 270. In the embodiment shown, the arm 300 has a jalapeno-shaped containment wall 301 that defines a bone stock space 302 into which the bone stock is initially deposited for cleaning. The bone stock space 302 moves with the arm 300 as the arm 300 oscillates between engaged and disengaged positions. The containment wall 301 is shaped to direct the bone stock into position between the arm 300 and the cutter 48 when the arm 300 moves to an engaged position.

Figure 11:
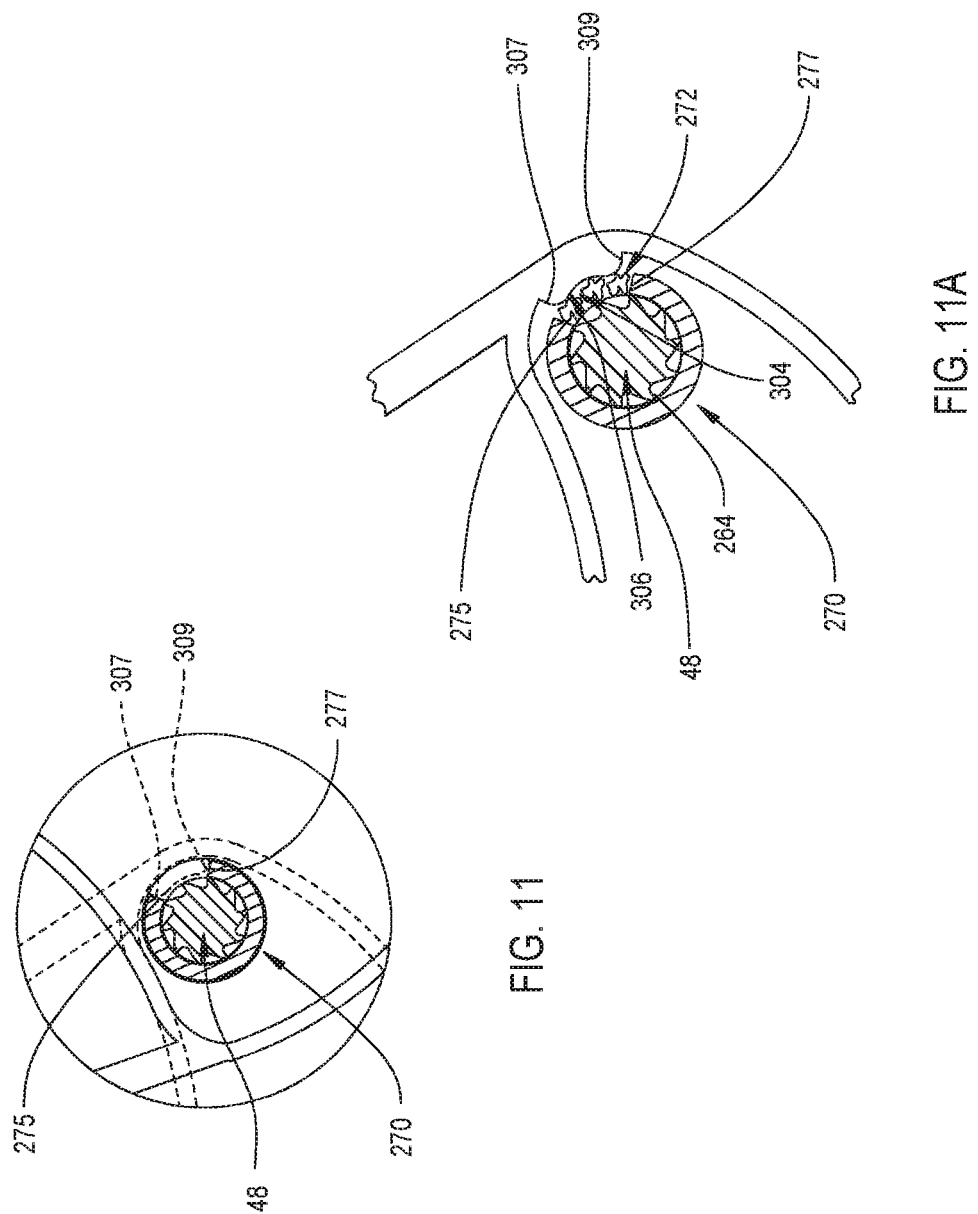
FIG. 11 is a close-up of FIG. 10 illustrating interaction between the cutter, shaving tube, and guide with a horizontal cross-section taken through the cutter and shaving tube.

FIGS. 10 and 11 shows arm 300 moving to an extreme clockwise position without any bone stock present in the bone stock space 302. FIG. 11A shows arm 300 in an engaged position. In the engaged position of FIG. 11A, the arm 300 is located so that bone stock is pressed into the shaving rotor 260 of cutter 48 by a press block 304 of the arm 300 through the cutter window 272. Front face 306 of press block 304 acts as a bearing surface that presses bone stock into cutter window 272 and against the cutting edges 264.

It should be appreciated that the arm 300 moves between a plurality of engaged positions and a plurality of disengaged positions. In essence, when the front face 306 of arm 300 is pushing bone stock into the cutter 48, the arm 300 is in an engaged position, even though the rotational position of the arm 300 may vary as more or less bone stock is located between the front face 306 and the cutter 48. When the arm 300 is located so that there is space between the front face 306 and cutter 48, such that the space is not being caused by bone stock trapped therebetween, then the arm 300 is in a disengaged position, i.e., no bone stock is engaged and being pressed into the cutter 48.

In a disengaged position, the arm 300 is located so that the bone stock is released from being pressed into the cutter 48 by the press block 304 so that the bone stock is provided an opportunity to be reoriented by the tumble plate 290. The bone stock is reoriented through continued rotation of the tumble plate 290, which, along with cutter 48, continues to rotate when the arm 300 is in engaged or disengaged positions, or moving therebetween. The bone stock is further reoriented by rotating the shaving tube 270 through one or more complete rotations about central axis A.

Front face 306 of press block 304 is configured to follow an arcuate path (not illustrated) to the cutter 48 when moving from a disengaged position to an engaged position. The arm 300 is shaped so that in an engaged position front face 306 faces the cutter 48 and containment wall 301 corrals the bone stock into position between the front face 306 and cutter 48 so that the bone stock is trapped and pressed into the cutter 48.

Arm 300 is periodically reciprocated between engaged and disengaged positions to reorient the bone stock trapped between the arm 300 and the shaving tube 270. The arm 300 pivots between engaged and disengaged positions about 5 to 20 times per minute. The speed at which the arm 300 pivots between engaged and disengaged positions is from 5 to 20 RPM. Movement of the arm 300 may be timed to the speed/motion of the shaving tube 270 so that the arm 300 is in an engaged position when the shaving tube 270 is actuated or when the shaving tube 270 is stationary. Likewise, the arm 300 is controlled so as not to pivot during some rotations of the shaving tube 270 when the arm 300 is in a disengaged position.

A biasing device such as a spring 278 (see FIG. 23A) biases the arm 300 toward an engaged position. When bone stock is present and becomes located between the front face 306 and the shaving rotor 260, then the spring 278 acts to press the arm 300 into the bone stock to push the bone stock against the cutter 48. Accordingly, the pressure exerted on the bone stock against the cutter 48 can be predetermined based on the size and properties of the spring 278.

If the bone stock should become piled or accumulate in such a way as to overcome the bias of spring 278 the bone stock would urge the arm 300 away from the cutter 48 against the bias of spring 278. The spring 278 may be an extension spring that acts to rotate arm 300 about axis A5 toward an engaged position. The force acting on the arm 300 via the spring 278 is transferred through the arm 300 to the bone stock. Should the opposing force from the bone stock to the arm 300 increase beyond the force of the arm 300 resulting from the spring 278, then the spring 278 is extended. As a result, the force acting on the bone stock is limited.

The spring 278 is associated with the arm 300 to act as a force limiting feature so that the force with which the arm 300 presses bone stock into the cutter 48 can be limited. The spring 278 limits damage to the osteoblastic progenitor layer of the bone stock by keeping the force applied to the bone stock in a range in which the osteoblastic progenitor layer remains substantially intact after the bone stock is cleaned. The specific force is dependent on geometry of cutter 48 and varies as the cutter geometry varies. For instance, with cutter geometry that more aggressively cuts material from the bone stock the force that could result in damage to the osteoblastic progenitor layer is less than with a cutter geometry that less aggressively cuts material from the bone stock. Thus, the force is tuned to the cutter geometry and is determined by identifying the force at which the osteoblastic progenitor layer remains substantially intact, but which still substantially cleans the bone stock.

When front face 306 engages or is at least in close proximity to shaving tube 270, but after some amount of bone cleaning takes place, shaving tube 270 may be rotated about central axis A to dislodge bone stock trapped therein. Arcuate side faces 307, 309 of press block 304 provide bearing surfaces against which trapped bone stock can bear as it is loosened or dislodged from cutter 48 and/or shaving tube 270 when the shaving tube 270 rotates.

Referring specifically to FIG. 11, the arcuate side faces 307, 309 of press block 304 abut corresponding side faces 275, 277 of the shaving tube 270 when the arm 300 is in an extreme clockwise position and no bone stock is present in the bone stock space 302 between the front face 306 and shaving rotor 260. The faces 307, 309, 275, 277 are shaped for abutting contact to prevent the front face 306 from intruding on the cutter 48 and to maintain a gap or spacing between the front face 306 and the cutter 48.

Figure 12:
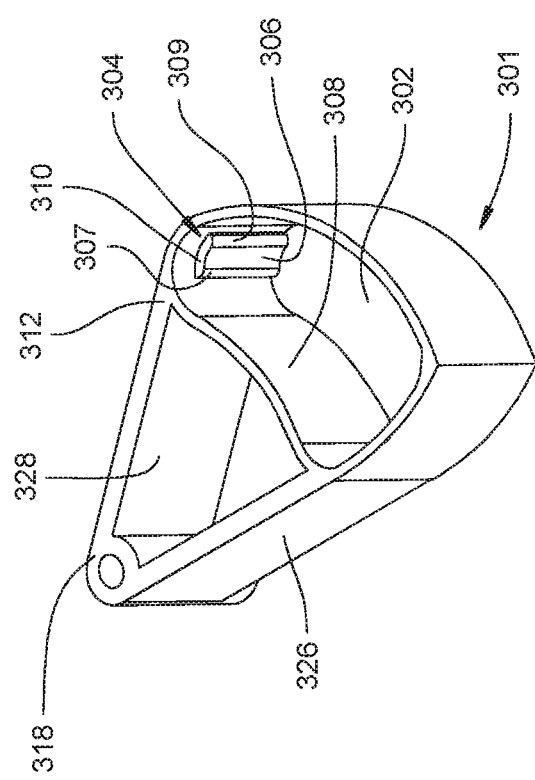
FIG. 12 is a top perspective view of the guide.
Figure 13:
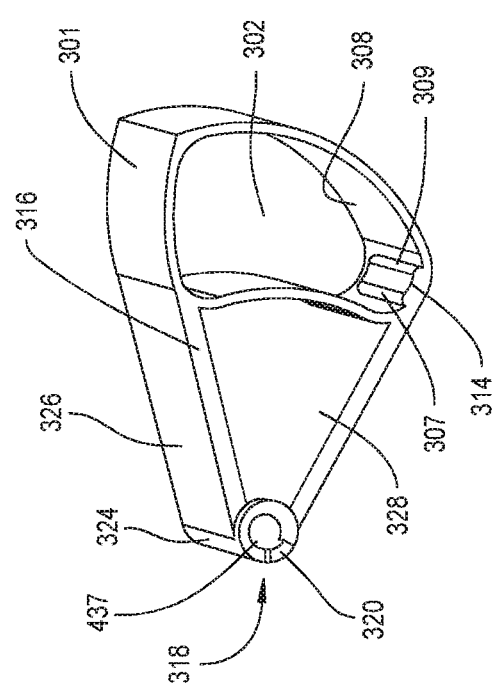
FIG. 13 is a bottom perspective view of the guide.

Arm 300 is shown separately in FIGS. 12 and 13. As shown, press block 304 protrudes inwardly from inner surface 308 of containment wall 301. Inner surface 308 defines the bone stock space 302. Front face 306 of press block 304 is arcuate in shape and interconnects arcuately shaped side surfaces 307, 309. Press block 304 has an upper surface 310 that is spaced below a top surface 312 of arm 300 (see FIG. 12). Press block 304 has a lower surface 314 that is coplanar with a bottom surface 316 of arm 300 (see FIG. 13).

Arm 300 includes a hub 318 pivotally mounted to cleaning module shell 250 about a hub pivot pin H (see FIG. 4) that is mounted to cleaning module top 249. Hub 318 is supported for pivotal movement about axis A5 to move arm 300 between disengaged and engaged positions. When the cleaning module 46 is positioned on top of the drive module 45, an interface tab 320 is positioned to be engaged by the gear train 201 so as to move the arm 300 between engaged and disengaged positions as described further below. The hub 318 has a semi-cylindrical or arcuate outer surface 324 defined between the top and bottom surfaces 312, 316 of arm 300. The arm 300 further includes wing walls 326, 328 connected to hub 318 and extending divergently from hub 318 to containment wall 301 to interconnect the hub 318 and the containment wall 301.

As shown in FIGS. 14-16, cutter 48 has a cylindrical intermediate shaft 251 extending downwardly from the shaving rotor 260. A bearing member B (see FIGS. 4 and 6) is located about intermediate shaft 251 to center intermediate shaft 251 and support rotation of the cutter 48 with shaving tube 270.

An axially lower stub shaft 254 with a non-circular cross section extends downwardly from the intermediate shaft 251. The lower stub shaft 254 is shaped to fit within a correspondingly shaped axial bore 255 in an axially upper section of drive gear 226. Owing to the non-circular geometry of the cross sections of lower stub shaft 254 and its receiving bore in drive gear 226, the cutter 48 and drive gear 226 are angularly fixed about central axis A for rotation together when engaged. When operating, the cutter 48 and drive gear 226 constantly rotate from 100 to 500 RPM.

Lower stub shaft 254 extends downwardly from intermediate shaft 251 to a chamfer 370. Lower stub shaft 254 is smooth and generally semi-cylindrical between opposing flats 256, which define the non-circular geometry of the cross-section.

The shaving rotor 260 of the cutter 48 is located axially above the intermediate shaft 251. The shaving rotor 260 is generally cylindrical and has an outer diameter that is larger than the diameters of the intermediate shaft 251 and lower stub shaft 254. The shaving rotor 260, intermediate shaft 251, and lower stub shaft 254 are integrally formed of metal, such as stainless steel.

A plurality of flutes 262 and corresponding cutting edges 264 are defined on shaving rotor 260. Upper 362 and lower 364 axial ends of shaving rotor 260 are flat and lie in planes perpendicular to central axis A. Flutes 262 and cutting edges 264 extend between the ends 362, 364. The flutes 262 and cutting edges 264 are arranged such that they helically wrap about shaving rotor 260 between ends 362, 364 and have a helix angle of from 20 to 70 degrees, or in some embodiments, from 30 to 60 degrees. In the embodiment shown, the cutter 48 has a helix angle of 60 degrees. An outside diameter of the shaving rotor 260 is ⅝ inches. The cutting edges 264 each have a rake angle of between −10 and 10 degrees. In the embodiment shown, the cutting edges 264 have a rake angle of 0 degrees. Ten flutes 262 are present in the cutter 48 shown in FIGS. 14-16.

Alternative embodiments of the cutter 48 are shown in FIGS. 14A-16A and 14B-16B. In FIGS. 14A-16A, the cutter 48A has a helix angle of 30 degrees. An outside diameter of the shaving rotor 260A is ⅝ inches. The cutting edges 264A have a rake angle of 0 degrees. Ten flutes 262A are present in the cutter 48A shown in FIGS. 14A-16A. In FIGS. 14B-16B, the cutter 48B has a helix angle of 45 degrees. An outside diameter of the shaving rotor 260B is ⅝ inches. The cutting edges 264B have a rake angle of 0 degrees. Ten flutes 262B are present in the cutter 48B shown in FIGS. 14B-16B.

Figure 17:
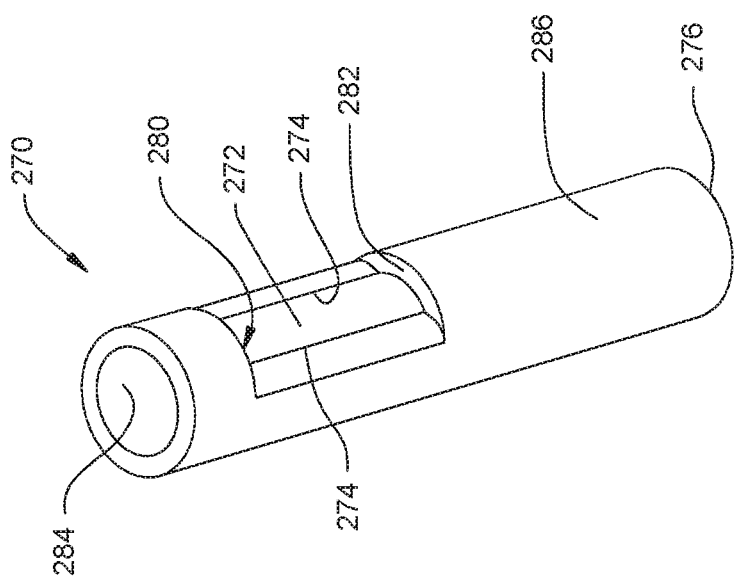
FIG. 17 is a top perspective view of the shaving tube.
Figure 18:
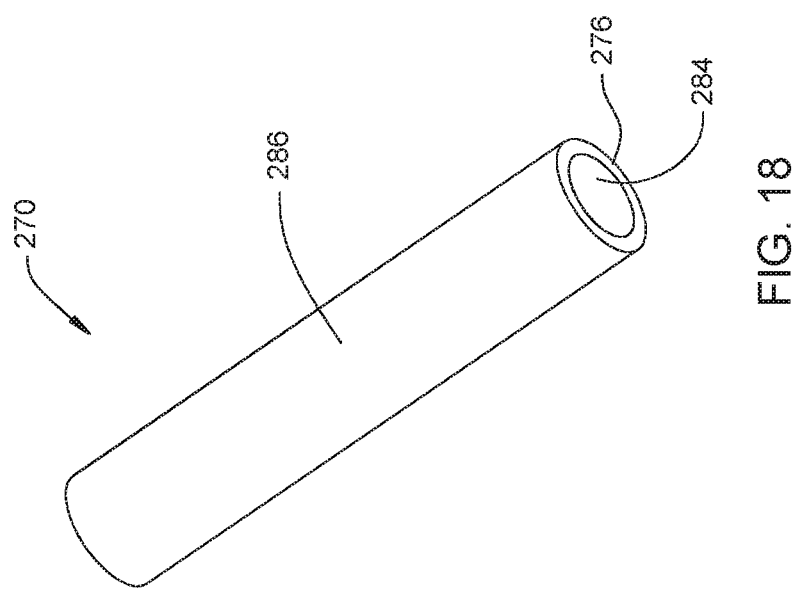
FIG. 18 is a bottom perspective view of the shaving tube.

Referring to FIGS. 17 and 18, shaving tube 270 is generally cylindrical and tubular for fitting over cutter 48. As shown in FIG. 17, the cutter window 272 creates the sharp shaver edges 274 capable of cutting soft tissue. A shaver edge 274 is located on both sides of the cutter window 272. Thus, the shaver edges 274 further define the sides of the cutter window 272. Surfaces 280, 282 at the top and bottom of the cutter window 272 are generally flat and parallel. A smooth shaft section 286 of the shaving tube 270 is located below the cutter window 272. The smooth shaft section 286 extends downwardly to a bottom end 276.

Shaver edges 274 are located so that soft tissue trapped between shaving rotor 260 and an inner cylindrical surface 284 of shaving tube 270 is cut by the shaver edges 274 either by action of the cutter 48 rotating relative to the shaving tube 270 when the shaving tube 270 is stationary or when the shaving tube 270 is rotating.

Figure 19:
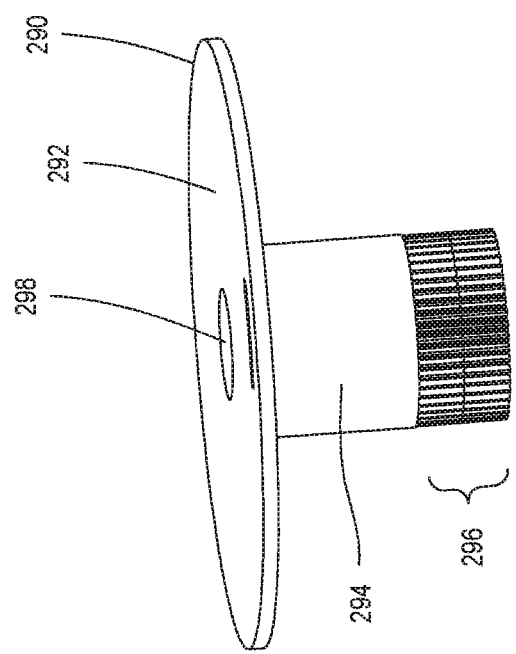
FIG. 19 is a perspective view of the tumble plate with integrated gear.
Figure 20:
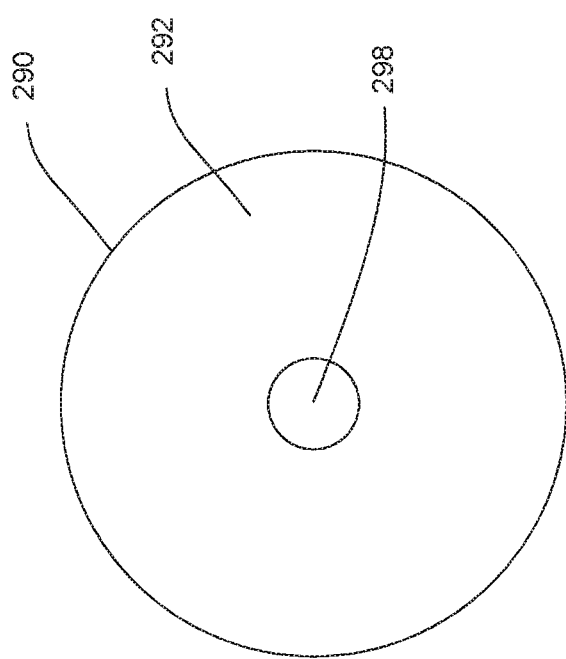
FIG. 20 is a top view of the tumble plate.

Tumble plate 290 is shown in FIGS. 19 and 20. The tumble plate 290 is generally circular and flat. Tubular shaft 294 is fixed to a bottom surface (not numbered) of tumble plate 290. The tubular shaft 294 extends downwardly from the tumble plate 290 and terminates in a gear section 296. A cylindrical passage 298 passes through the tumble plate 290, tubular shaft 294, and gear section 296. As shown in FIG. 6, the cylindrical passage 298 is sized to accommodate the shaving tube 270, cutter 48, and bearing member B. In the embodiment shown, the bearing member B is a bushing press fit into the shaving tube 270 to rotate therewith. Gear section 296 is operatively coupled to the drive gear 226 when the cleaning module 46 is fitted onto the drive module 45 and connected thereto.

Figure 21:
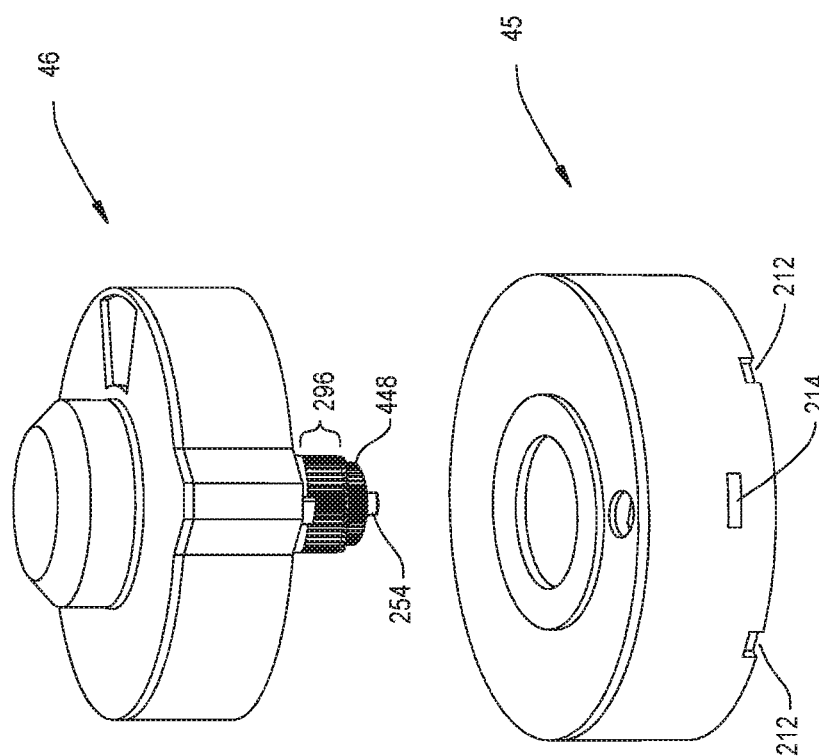
FIG. 21 is an exploded perspective view of the cleaning module and drive module showing their alignment for connection.

Referring to FIGS. 21 and 22, when the cleaning module 46 is connected to the drive module 45, the gear train 201 of drive module 45 is capable of transferring torque received from base unit motor 44 to the cutter 48, shaving tube 270, tumble plate 290, and arm 300 of the cleaning module 46. In the embodiment shown, the cleaning module 46 is provided as a disposable unit designed to be utilized for one bone cleaning session and then discarded, while the drive module 45 is provided as a reusable unit designed to be sterilized and reused.

Referring to FIGS. 22-26, gear train 201 is located in the lower cavity 218 of shell 200. The gear train 201 includes the drive gear 226. When shell 200 is received in mounting space 64 of pedestal 58, drive gear 226 engages the spindle head 90. Driving torque is transferred from the spindle head 90 to the drive gear 226 upon actuation of the base unit motor 44.

When the cleaning module 46 is connected to the drive module 45, several connections are made. In one such connection, the lower stub shaft 254 of cutter 48 is inserted into the correspondingly shaped axial bore 255 of drive gear 226. In another connection, the gear section 296 of tubular shaft 294, which is fixed to the tumble plate 290, engages a coupler gear 401 (see FIG. 6). The coupler gear 401 includes a lower spur gear 402 directly driven by drive gear 226 that also engages and drives the gear section 296. These connections establish an operative coupling between the base unit motor 44 and cutter 48/tumble plate 290 such that when the base unit motor 44 is actuated, drive gear 226 rotates cutter 48 and tumble plate 290 in unison about central axis A.

An upper spur gear 404 of coupler gear 401 is centrally fixed to the lower spur gear 402 to rotate therewith about the same central axis A2, which is fixed relative to the shell 200. Thus, when the lower spur gear 402 is driven by the drive gear 226, the upper spur gear 404, albeit of smaller diameter, is likewise driven.

A speed reducing gear 406 engages the upper spur gear 404 to be driven thereby. The speed reducing gear 406 has a lower spur gear 408 and an upper spur gear 410 of smaller diameter. The upper spur gear 410 of speed reducing gear 406 is centrally fixed to the lower spur gear 408 of speed reducing gear 406 to rotate therewith about the same central axis A3, which is fixed relative to the shell 200.

A cam gear 412 engages the speed reducing gear 406 so that rotation of the speed reducing gear 406 results in rotation of the cam gear 412. The cam gear 412 has a cam spur gear 414 that engages the upper spur gear 410 of speed reducing gear 406 to be driven by the upper spur gear 410. The speed reducing gear 406 reduces the rotational speed input from coupler gear 401.

Cam gear 412 includes a cam plate 416 having a non-circular, cam-shaped, perimeter. The perimeter has a cam outer surface 418 perpendicular to the cam spur gear 414. The cam plate 416, when viewed from above, has a semi-circular section 420 joined by a cam section 422 (see FIG. 24). The cam section 422 protrudes radially outwardly from a cam gear axis A4 further than the semi-circular section 420 (see FIG. 24). The cam gear axis A4 is fixed relative to the shell 200.

When cam spur gear 414 is driven by the upper spur gear 410 of speed reducing gear 406, cam spur gear 414 rotates about cam gear axis A4. Owing to being fixed to the cam spur gear 414, cam plate 416 likewise rotates.

A cam follower 426 couples the arm 300 to the gear train 201. Cam follower 426 has a generally cylindrical body (not numbered) with upper and lower surfaces (not numbered). A post 428 is integrally formed with the body and extends downwardly from the lower surface. Post 428 is configured to generally follow along the cam outer surface 418 (although not shown, the post 428 may include an outer bearing that rolls along the cam outer surface 418).

A second post 429 is integrally formed with the body and extends downwardly from the lower surface at a location spaced from the post 428. Both posts 428, 429 are spaced radially outwardly from axis A5 (also referred to as cam follower axis A5). One end of spring 278 is attached to the second post 429. The other end of spring 278 is mounted to an inner surface of outer wall 204 of shell 200 so that the spring 278 (in this case an extension spring) is constantly biasing the cam follower 426 clockwise (viewed from above).

The cam follower 426 also has a cam interface tab 430 configured to engage hub interface tab 320, as shown in FIG. 23A (shown without hub pivot pin H). The cam interface tab 430 is part of the drive module 45, while the hub interface tab 320 is part of the cleaning module 46. The cam interface tab 430 has a first side surface S1 and a second side surface S2. The first side surface S1 is configured to abut a third side surface S3 of hub interface tab 320. When the first and third side surfaces S1, S3 abut, the first and third side surfaces S1, S3 are parallel to one another.

A torsion spring 435 is seated within a bore 437 located in the hub 318. Torsion spring 435 has two tangs 439a, 439b. Tang 439a abuts second side surface S2 of cam interface tab 430 upon connection of cleaning module 46 to drive module 45. Tang 439b abuts an inner surface 327 of wing wall 328. Thus, torsion spring 435 acts to urge arm 300 counterclockwise relative to cam follower 426.

Figure 23C:
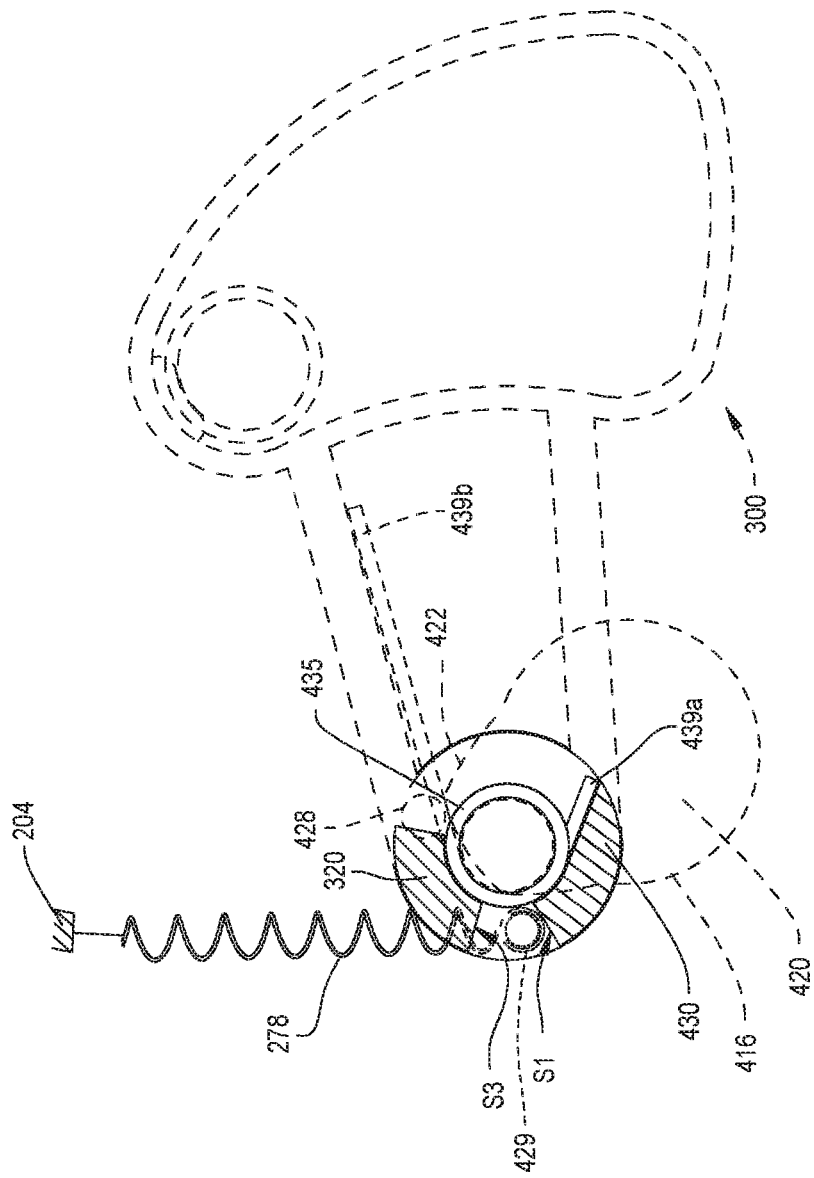

FIGS. 23B through 23E show movement of the cam plate 416 and corresponding movement of the cam follower 426. FIG. 23B shows the cam interface tab 430 engaging the hub interface tab 320 and together the arm 300 and cam follower 426 are biased into an extreme clockwise position under the tension of spring 278. Post 428 is contacting the semi-circular section 420 of the cam plate 416. This positional configuration occurs when no bone stock is trapped between the front face 306 and cutter 48, i.e., no bone stock is being cleaned.

In FIG. 23C, as the cam plate 416 rotates, the post 428 moves to the cam section 422 of cam plate 416 from the semi-circular section 420, thereby rotating the cam follower 426 counterclockwise (viewed from above). Since the cam section 422 extends radially further away from the cam gear axis A4 than the semi-circular section 420, the cam follower 426 is rotated counterclockwise about the cam follower axis A5. The cam follower axis A5 is fixed relative to the shell 200.

When this movement of the cam follower 426 occurs, the tang 439a of torsion spring 435 is wound toward the tang 439b. The arm 300 is thus urged to follow the movement of the cam follower 426 via the tang 439b, but FIG. 23C shows a delayed reaction of the arm 300, which results in a gap forming between the first and third side surfaces S1, S3. This delayed reaction can either be from slow reaction of the torsion spring 435 or perhaps bone stock is trapped between the arm 300 and shaving tube 270 preventing counterclockwise rotation of the arm 300.

Figure 23D:
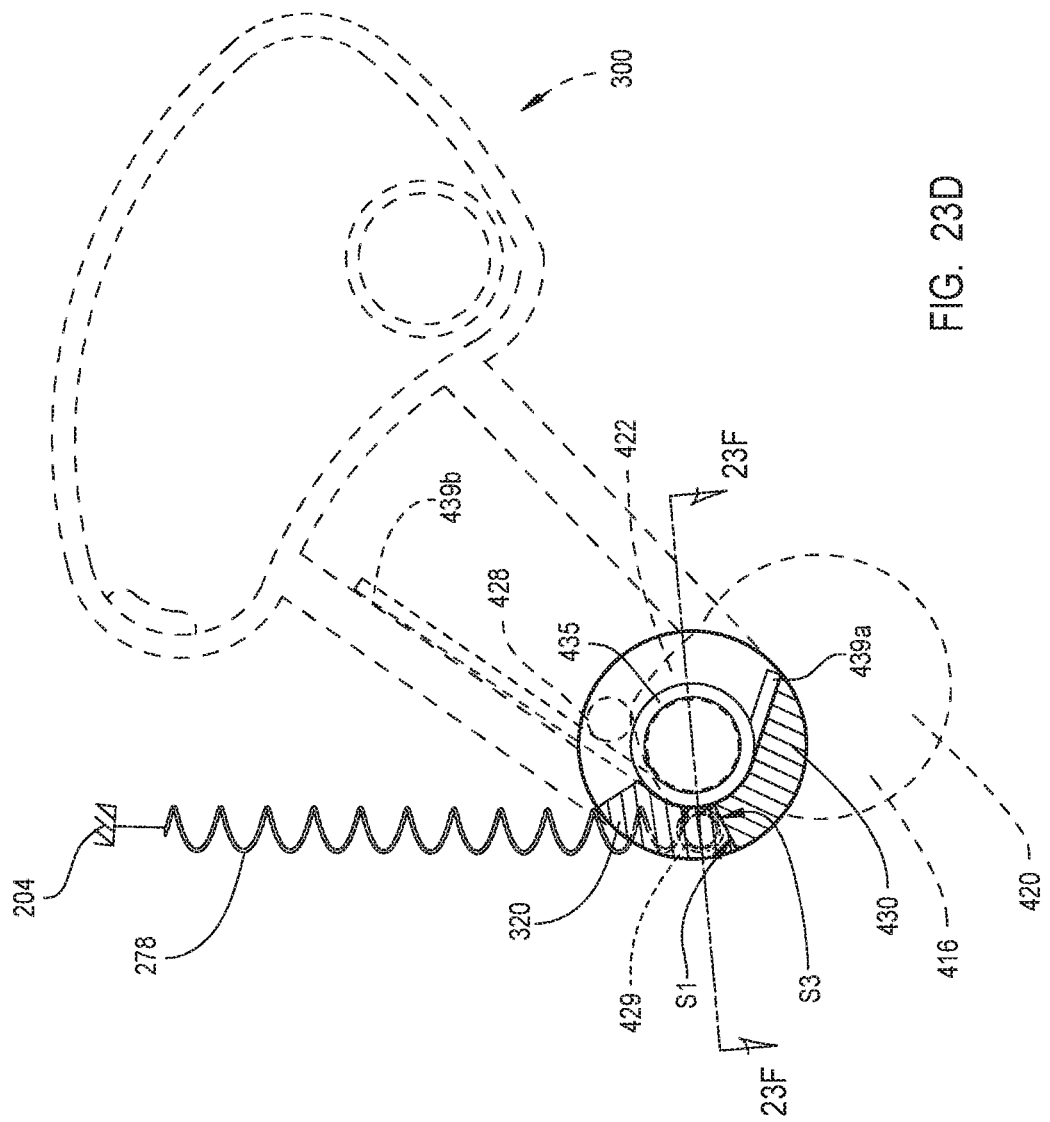

FIG. 23D shows the arm 300 rotationally catching up with the cam follower 426 under the torque created by torsion spring 435 resulting in the third side surface S3 abutting the first side surface S1. The arm 300 is thus moved to disengaged positions via the torsion spring 435. The torsion spring 435 acts to bias arm 300 counterclockwise such that containment wall 301 engages the shaving tube 270. Accordingly, the containment wall 301 can act as a bearing surface to loosen material when the shaving tube 270 rotates. In FIG. 23D, the post 428 continues to follow along the cam section 422 of the cam plate 416. In FIGS. 23C and 23D, the spring 278 acts to bias the post 428 of the cam follower 426 against the outer surface 418 of the cam plate 416 when the post 428 follows around the cam section 422 of the cam gear 412. The spring 278 is extended in these positions compared to the extension of spring 278 in FIG. 23B.

FIG. 23E shows the cam plate 416 rotating back to a position in which the semi-circular section 420 is adjacent to the post 428. When this occurs, if there was no bone stock between the front face 306 and the cutter 48 the arm 300 would move to the fully clockwise position under the bias of spring 278, which would also rotate the cam follower 426 clockwise such that the post 428 contacted the outer surface 418 of the cam plate 416 on the semi-circular section 420. However, FIG. 23E depicts a typical cleaning situation in which bone stock is trapped between the front face 306 and the cutter 48 and is being cleaned by the cutter (see FIG. 11A). Thus, the arm 300 is impeded by the bone stock, which opposes the force provided by spring 278. As a result, the arm 300 is unable to rotate completely into the fully clockwise position abutting shaving tube 270. Instead, the arm 300 is in an engaged position in which the trapped bone stock is being pressed into the cutter 48. The trapped bone stock causes the arm 300 to be spaced from the shaving tube 270 and cutter 48. Owing to the abutting first and third surfaces S1 and S3, cam follower 426 is also not allowed to fully rotate clockwise such that the post 428 is spaced from (or lifted off) the outer surface 418 of the cam plate 416.

Cam follower 426 and hub 318 of arm 300 pivot about cam follower axis A5, as shown in FIG. 23F. A bearing member B may be located between the cam follower 426 and top 216 of shell 200 to allow rotation of the cam follower 426 in the top 216. Similarly, a bearing member B is located between hub 318 and cleaning module base 245 to allow rotation of hub 318 in the cleaning module base 245.

When the cleaning module 46 is placed on the drive module 45, the hub pivot pin H centers into a central bore (not numbered) in the cam follower 426 to align the cam follower 426 to the hub 318.

Referring back to FIG. 22, an indexing gear 432 is disposed for rotation about indexing central axis A6 in shell 200. The indexing central axis A6 is fixed relative to shell 200. The indexing gear 432 includes an indexer spur gear 434. An indexing plate 436 is fixed to an upper surface of the indexer spur gear 434. The indexing plate 436 defines a plurality of indexing grooves 438. Four indexing grooves 438 are provided in the embodiment shown. The indexing grooves 438 are equally circumferentially located every 90 degrees about the indexing central axis A6. Indexing grooves 438 start at a position spaced from indexing central axis A6, are elongated in a radial direction therefrom, and terminate short of outer perimeter of indexer spur gear 434.

Figure 25:
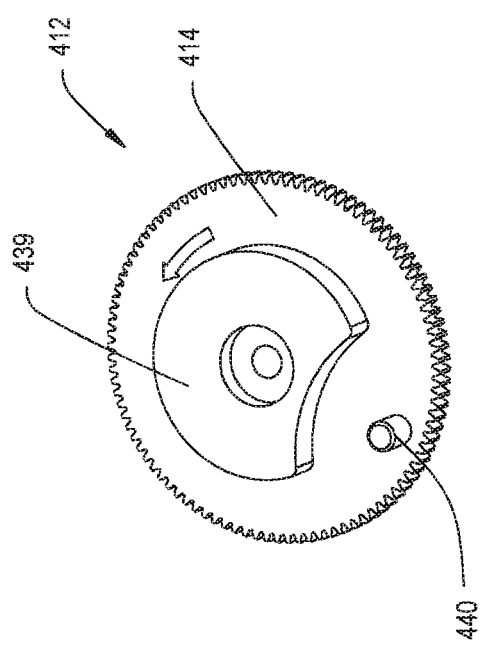
FIG. 25 is a bottom perspective view of the cam gear showing an indexer pin that cooperates with the indexing gear.
Figure 26:
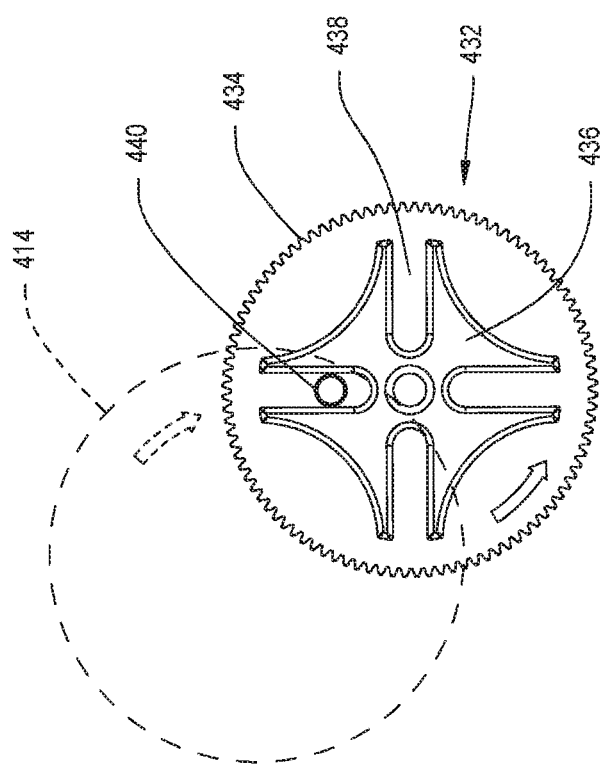
FIG. 26 is a top view of the indexing gear illustrating operation of the indexer pin sliding in an indexing groove in the indexing gear.
Figure 27:
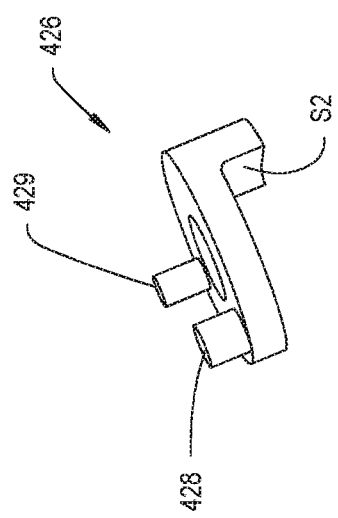
FIG. 27 is a bottom perspective view of a cam follower.
Figure 28:
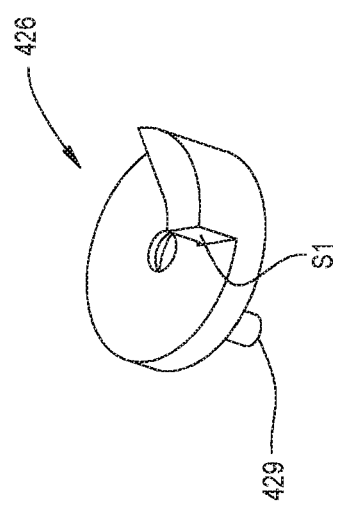
FIG. 28 is a top perspective view of the cam follower.
Figure 29:
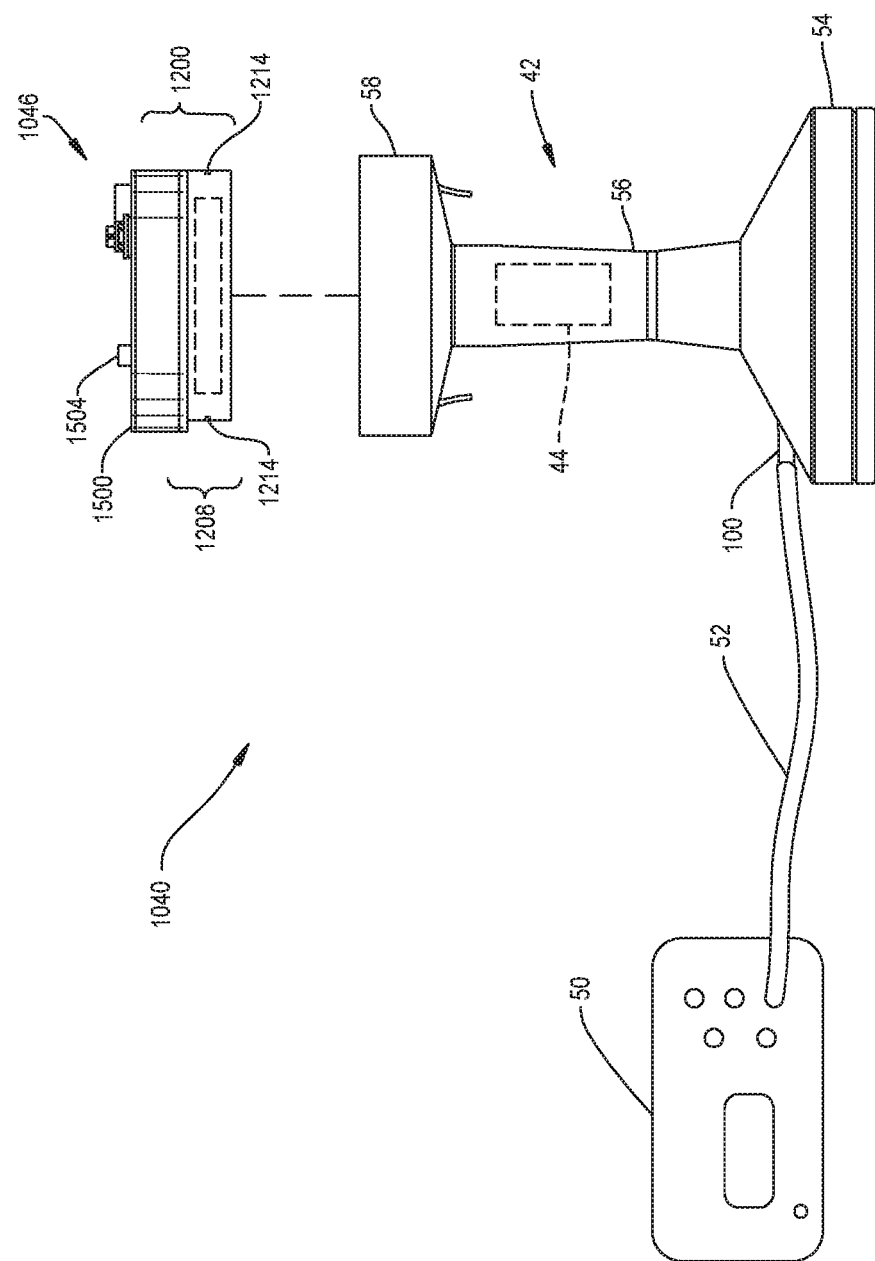
FIG. 29 is an elevational view of an alternative system for cleaning bone stock.

An indexer pin 440 depends downwardly from a bottom surface of cam spur gear 414 (see FIG. 25). The indexer pin 440 is spaced radially inwardly from a perimeter of the cam spur gear 414, yet radially outwardly from the cam gear axis A4. When cam spur gear 414 is driven, indexer pin 440 rotates about cam gear axis A4. The indexer pin 440 is configured to engage the indexing plate 436 and slide into the indexing grooves 438. For every one rotation of the cam spur gear 414, the indexer pin 440 engages one indexing groove 438 and rotates the indexing gear 432 one-quarter of a turn or 90 degrees about indexing central axis A6. This arrangement is conventionally referred to as a geneva drive in which the cam spur gear 414 is a drive wheel and the indexing gear 432 is a driven wheel. A blocking disc 439 of this geneva drive is shown in FIG. 25. The blocking disc 439 locks the driven wheel in position between steps.

A tube gear 442 engages the indexer spur gear 434 to be driven thereby about tube gear axis A7. The tube gear 442 has a lower spur gear 444 and an upper spur gear 446 of smaller diameter. The upper spur gear 446 is centrally fixed to the lower spur gear 444 to rotate therewith about the same tube gear axis A7, which is fixed relative to the shell 200. The upper spur gear 446 engages the indexer spur gear 434 to be periodically driven by the indexer spur gear 434, as dictated by the geneva drive. Lower spur gear 444 engages ring-shaped spur gear 448.

The bottom end 276 of shaving tube 270 is press-fit into the ring-shaped spur gear 448 to rotate with rotation of the ring-shaped spur gear 448. The ring-shaped spur gear 448 is thus part of the cleaning module 46 in the embodiment shown. In other embodiments, the ring-shaped spur gear 448 forms part of the drive module 45.

Ring-shaped spur gear 448 is rotatable relative to the drive gear 226 about central axis A. In another connection made when the cleaning module 46 is mounted to the drive module 45, the ring-shaped spur gear 448 engages lower spur gear 444. The tube gear 442 is configured so that one quarter turn of the indexer spur gear 434 results in one complete rotation of 360 degrees of the ring-shaped spur gear 448 and shaving tube 270.

Pivot pins P having heads and threaded ends are used to secure the coupler gear 401, speed reducing gear 406, cam gear 412, indexing gear 432, and tube gear 442 to the shell 200 of drive module 45. In the embodiment shown top 216 of shell 200 includes internally threaded bosses to which the pivot pins are attached (see, e.g., FIG. 6). A similar boss is located on cleaning module top 249 to receive hub pivot pin H (pivot pin with threaded end, but without head) for rotatably supporting the hub 318. Spacers S may be provided about pivot pins P to space certain gears from top 216 as appropriate (see FIG. 6). The gears 401, 406, 412, 432, 442, cam follower 426, and hub 318 are configured to rotate about the pins P, H, which define axes A2-A7. These axes A2-A7 are also fixed in relation to each other and parallel to one another.

II. Operation

During operation, uncleaned bone is first placed in the void space 252/bone stock space 302 for cleaning and the lid 500 is then rotated into place relative to cleaning module shell 250 via slide handle 504 to cover the void space 252. The uncleaned bone includes soft tissue attached thereto that requires removal without damaging the periosteum layer.

The cleaning module 46 is then fitted to the drive module 45, after the drive module 45 is releasably locked to the base unit 42. In some embodiments, the uncleaned bone is placed in the void space 252/bone stock space 302 after these steps.

The surgical personnel actuate the cleaning module 46 by depressing the push button of base unit switch 98. In response to the depression of switch 98 the motor controller (not illustrated) causes power to be applied to the motor 44, which energizes the motor 44 and causes its output shaft 78 to turn in a direction that drives rotation of cutter 48 counterclockwise as viewed from above.

The tumble plate 290 rotates in unison with the cutter 48 in the counterclockwise direction. Tumble plate 290 operates to move the bone stock so that the bone stock is ultimately positioned between the front face 306 of press block 304 and cutter 48. In the engaged position, front face 306 presses the bone stock toward shaving rotor 260 of cutter 48 through window 272 in shaving tube 270 to cut soft tissue from the bone stock.

The cutting edges 264 of shaving rotor 260 and/or shaver edges 274 of shaving tube 270 cut away soft tissue from bone. The cut soft tissue and other debris is then augered upwardly between the shaving rotor 260 and shaving tube 270. The augered tissue is stored for later retrieval or disposal. This provides a separation of soft tissue and other debris from the remaining bone of the bone stock.

After some amount of bone cleaning takes place, gear train 201 is configured to rotate shaving tube 270 about central axis A to dislodge bone stock trapped therein. The arm 300 provides a bearing surface against which trapped bone stock can bear as it is loosened or dislodged from cutter 48 and/or shaving tube 270 when the shaving tube 270 rotates—with the arm 300 in either engaged or disengaged positions, and sometimes when the arm 300 is in an extreme counterclockwise position (see FIG. 23D). The gear train 201 is configured so that the shaving tube 270 rotates about central axis A between 0 and 360 degrees once every 1 to 5 seconds with alternating periods without rotation in which arm 300 is actively pressing bone stock into cutter 48 through the window 272.

During cleaning, gear train 201 periodically pivots arm 300 between the engaged and disengaged positions to reorient the bone stock trapped between the arm 300 and the cutter 48/shaving tube 270. The arm 300 pivots between the engaged and disengaged positions about 5 to 20 times per minute. This further facilitates removal of soft tissue and debris from all surfaces of the bone stock.

Once the cleaning module 46 has sufficiently removed soft tissue from the bone, the bone is removed from the cleaning module 46. In one embodiment, the lid 500 is rotated by slide handle 504 to expose opening 506. Next, the cleaned bone is grabbed by forceps or other device (not illustrated) to be placed in a collection tray for further processing. In other embodiments, not shown, the bone is gathered automatically into the collection tray (not illustrated), which is then removed from the drive module 45 or the cleaning module 46—depending on which module is used to hold the collection tray.

At the conclusion of the cleaning process, the cleaning module 46 is removed from the drive module 45. Drive module 45 is also released from base unit 42. The cleaning module 46 may then be discarded (or cleaned in some embodiments). The drive module 45 and base unit 42 are then cleaned for reuse.

One advantage of the system 40 is that it provides a mechanized and automated manner of cleaning the bone stock that substantially reduces the need for surgical personnel to grasp and clean the bone manually.

Likewise it should be understood that while this invention is intended for use to clean autograft bone, its applications are not so limited. System 40 of this invention may also be used to clean donor bone, sometimes referred to as allograft bone, or to clean or process other materials.

III. Alternative Embodiments

In some embodiments, the components of the drive module 45 are integrated into the base unit 42. In these embodiments, the cleaning module 46 connects directly to the base unit 42. In yet other embodiments, the components of the drive module 45 are integrated into the cleaning module so that the gear train 201 forms part of the cleaning module.

In some embodiments, rotation of the shaving tube 270 occurs in alternating clockwise and counterclockwise directions. Oscillating movement of the shaving tube 270 helps to dislodge and release bone stock caught between the shaving rotor 260 and shaving tube 270. In yet other embodiments, the shaving tube 270 may be rotated less than 360 degrees, such as from 90 to 270 degrees. Further, constant or periodic oscillation of shaving tube 270 about central axis A could be employed. Alternatively, constant rotation of shaving tube 270 in the same direction could be employed to dislodge trapped bone stock. The drive module 45 can be configured for any of these scenarios, or any combination thereof.

In some embodiments, when arm 300 is in the engaged position, but after some amount of bone cleaning takes place, shaving tube 270 may be rotated completely about central axis A to dislodge bone stock trapped therein. In other embodiments, when the arm 300 is in the extreme counterclockwise position (see FIG. 23D), a projection (not illustrated) on inner surface 308 of arm 300, opposite the press block 304, provides a bearing surface against which trapped bone stock can bear as it is loosened or dislodged from cutter 48 and/or shaving tube 270 when the shaving tube 270 rotates.

The materials from which the components of this invention are fabricated and the geometry of the components may be different from what has been described. For example, in embodiments of the invention having components intended to be disposable, some or all of those components may be made of sterilizable plastic instead of being made of metal. In certain embodiments, the cutter 48, shaving tube 270, bearing members B, and gears are formed of metal such as stainless steel, while the shells 200, 250, tumble plate 290, and arm 300 are formed of sterilizable plastic. In some embodiments the gears are also formed of sterilizable plastic. In some embodiments the cutter 48 and shaving tube 270 are also formed of sterilizable plastic.

It is envisioned that in another alternative embodiment, the drive module 45 includes a separate, reversible stepper or servo motor (not illustrated) mounted to the shell 200 that directly drives the drive gear 226, and the required controls are mounted to the shell 200. Accordingly, the drive module 45 does not require mounting to the base unit 42.

It is further envisioned that in alternative embodiments, the gear train 201 includes a separate reversible stepper or servo motor (not illustrated) mounted to shell 200 that directly drives the arm 300, separately from the cutter 48, shaving tube 270, and tumble plate 290. This motor includes an output shaft connected directly to the hub 318. In this embodiment, the force limiting feature that limits damage to the osteoblastic progenitor layer is integrated in the control unit to the arm motor. More particularly, force is limited by sensing motor current and adjusting motor voltage to maintain motor current below a predetermined set point corresponding to a given torque. The selected torque is determined based on the relationship between torque and damage to the osteoblastic progenitor layer. The selected torque removes unwanted material from the bone stock yet substantially maintains the osteoblastic progenitor layer.

Power may be supplied to the base unit motor 44, in some embodiments, by a battery powered control unit (not illustrated). The battery powered control unit supplies electrical energization signals to the base unit motor 44 to actuate the base unit motor 44. The battery powered control unit is integrated into the base unit 42. Additionally, power received from console 50 through cable 52 and socket 100 or from the battery powered control unit is regulated by the motor controller and provided to the windings of base unit motor 44 when switch 98 is electrically closed. Power to the base unit motor 44 may be provided continuously when the push button is actuated, and then discontinued when the push button 98 is actuated a second time, or power may be provided for a predetermined period of time such as 2 minutes after actuation of the push button 98. Alternatively, the push button 98 may be a rocker switch having on and off positions.

In some embodiments, flutes on the cutter have shapes other than helical, such as vertical flutes. Additionally, the cutter may have less flutes or more flutes. The flutes may have a larger or smaller helix angle. The cutter may also have cutting edges with a larger or smaller rake angle.

In some embodiments, the shaver edges may be blunt so as to provide impingement to sever soft tissue caught between the shaving rotor 260 of cutter 48 and the shaving tube when the shaving rotor 260 rotates relative to the shaving tube.

IV. Alternative Cleaning Module

Referring to FIGS. 29-50, an alternative cleaning module 1046 is shown. Alternative cleaning module 1046 includes a shell 1200. Shell 1200 is dimensioned to fit to the base unit 42 so that the base unit motor 44, when actuated, drives cutter 1048. Shell 1200 defines a void space 1202 for receiving harvested and uncleaned bone stock. During use, cutter 1048 cleans the bone stock in the shell void space 1202 by cutting soft tissue and other debris from the bone stock.

Shell 1200 has a base 1208. Shell base 1208 includes a lower wall 1210. Shell base lower wall 1210 has an outer periphery that allows the shell 1200 to be slip fitted into the void space 164 above pedestal top surface 60 and within lip 62. Shell base lower wall 1210 is coterminous with lip 62 on both sides of notch 68 so that shell base lower wall 1210 is semi-cylindrical.

Figure 31:
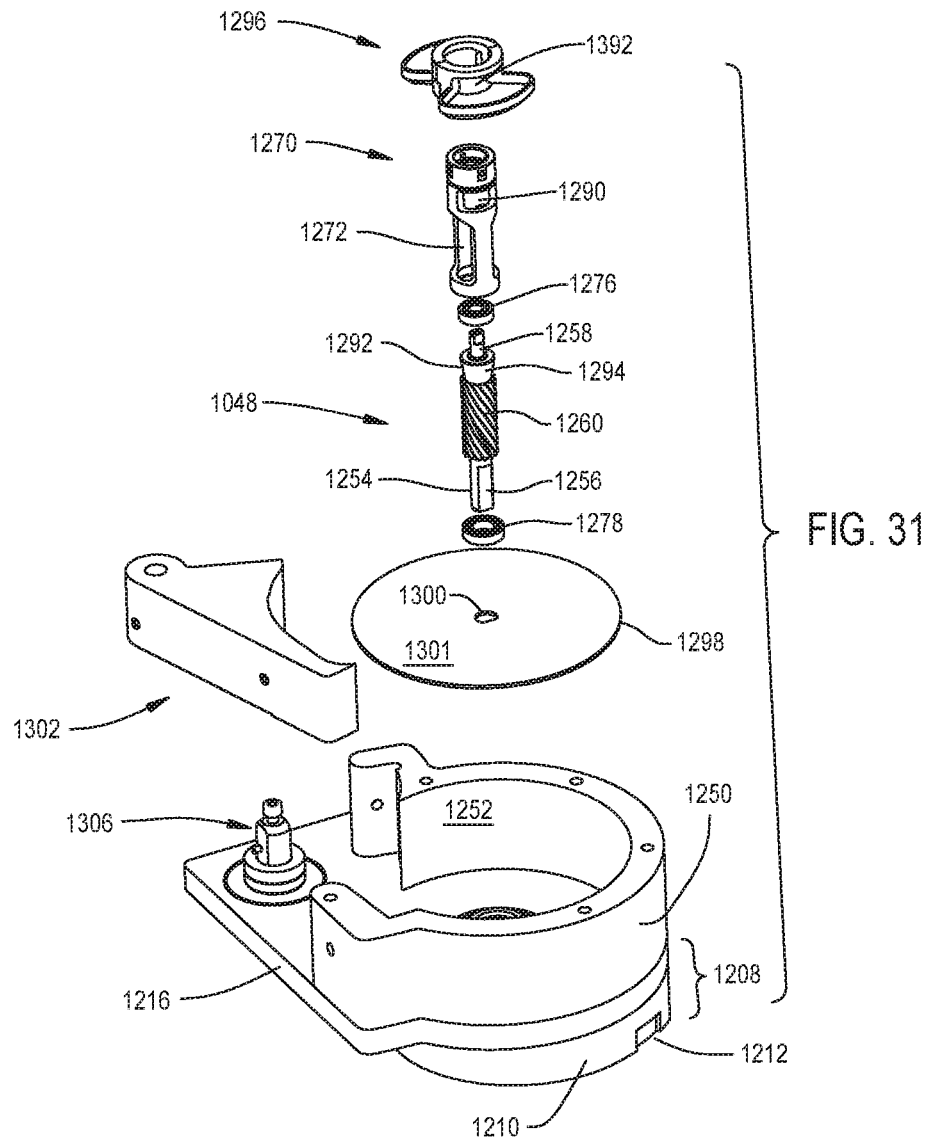
FIG. 31 is an exploded perspective view of the alternative cleaning module.
Figure 32:
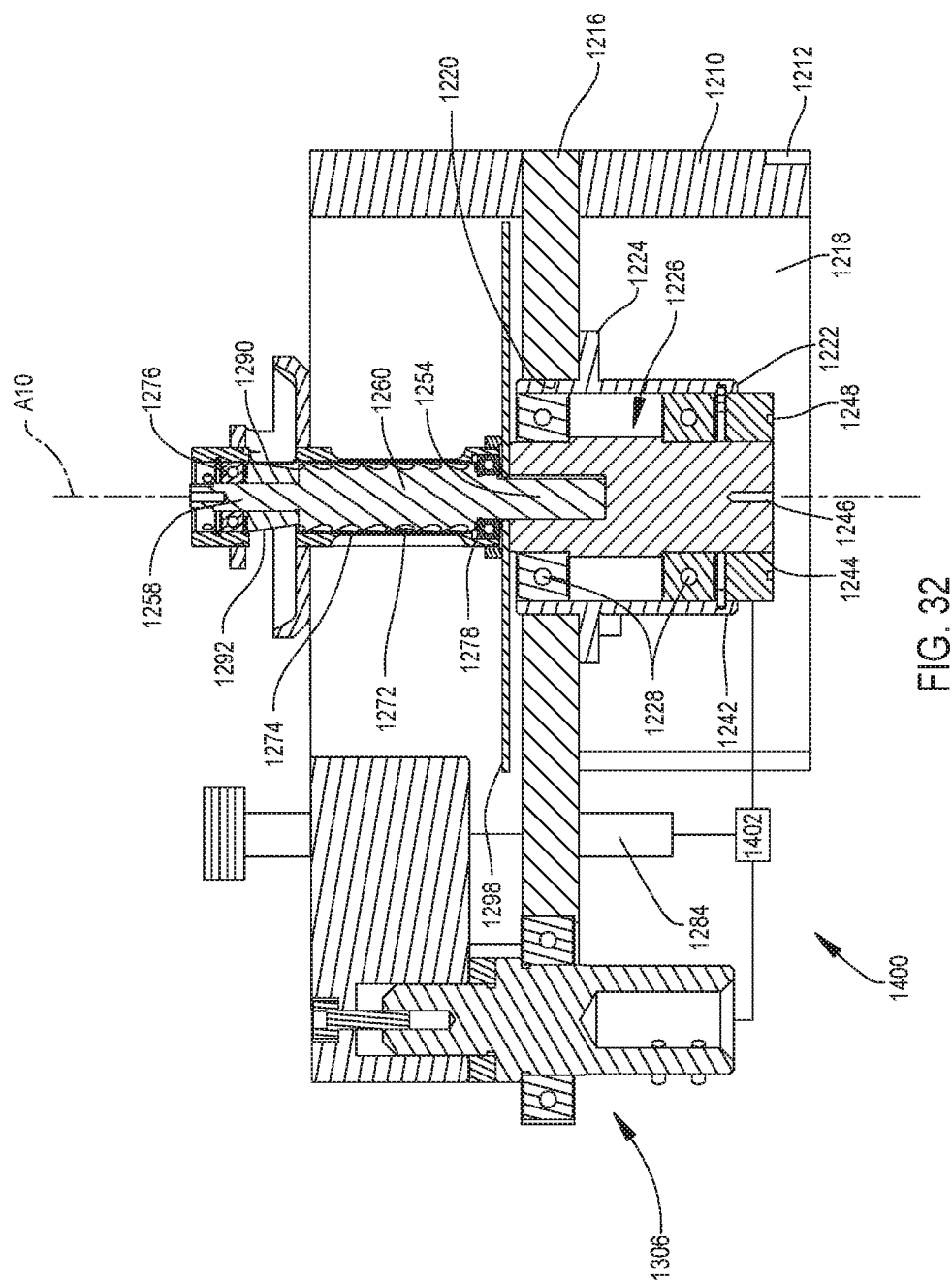
FIG. 32 is a cross-sectional view of the alternative cleaning module.

Four circumferentially and equiangularly spaced apart notches 1212 extend radially inward in, and axially upward from, a downwardly directed face of the base lower wall 1210 (only one notch is shown in FIGS. 31 and 32). Notches 1212 are dimensioned so that when the shell 1200 is fitted to base unit 42, pedestal teeth 70 are seated in the notches 1212. Engagement of the teeth 70 and notches 1212 prevents unwanted rotation of the shell base 1208 relative to the base unit 42 during operation.

Shell base lower wall 1210 is further provided with two additional side notches 1214 (see FIG. 29) that are diametrically opposed from each other. Side notches 1214 extend radially inwardly from an outer cylindrical surface of the base lower wall 1210 at a location above the bottom of the base lower wall 1210. More particularly, shell 1200 is formed so that when the shell 1200 is seated in pedestal void space 64 and teeth 70 are seated in notches 1212, side notches 1214 are positioned to receive the radially inwardly directed fingers 74 of retention arms 72. The fingers 74 are biased radially inwardly to seat against cooperating surfaces of the side notches 1214 to selectively lock shell 1200 to base unit 42. The upper surfaces of fingers 74 may be downwardly angled radially inwardly. This allows shell 1200 to slidably engage and move fingers 74 radially outward against the biasing force acting on retention arms 72. Thus, shell 1200 may be pushed downwardly past the fingers 74 and received in void space 64 without levers 76 being manually actuated.

Shell base 1208 further includes a base plate 1216 mounted to base lower wall 1210. Shell base lower wall 1210 extends downwardly from base plate 1216 to define a lower cavity 1218 of shell 1200. Shell lower cavity 1218 has a diameter that is larger than the diameter of spindle head 90. This allows the spindle head 90 to be received in the lower cavity 1218.

A center opening 1220 is defined in and through the base plate 1216. A support tube 1222 is mounted to the base plate 1216 and has an upper end that is received in center opening 1220. A lower end of support tube 1222 projects into lower cavity 1218. The support tube 1222 includes a flange 1224 located between the upper and lower ends of the support tube 1222. Flange 1224 is fixed to the bottom surface of the base plate 1216 by welding, fasteners (not illustrated), ultrasonic welding, adhesive, or the like.

A coupler shaft 1226 is supported to rotate within the support tube 1222. Bearings 1228 are positioned inside support tube 1222 to rotatably support the coupler shaft 1226. The coupler shaft 1226 is tubular in shape and has an axially upper section and an axially lower section, which are separated by an axially intermediate section (sections not numbered). Bearings 1228 are disposed about the upper and lower sections. Upper and lower sections have a common diameter. The diameter of intermediate section is relatively larger than that of upper and lower sections. Owing to its larger diameter, intermediate section defines opposing annular shoulders by which the bearings 1228 are axially spaced and against which they respectively abut.

An annular groove (not separately numbered) is formed in an inner cylindrical surface of the support tube 1222. Groove is located near but axially spaced from the lower end of the support tube 1222. A retaining ring 1242 is seated in the groove and projects radially inwardly from the tube's cylindrical wall. The lowermost bearing 1228 axially abuts retaining ring 1242 which limits the downward movement of that bearing 1228 and coupler shaft 1226 within support tube 1222. Thus, the bearings 1228 and the coupler shaft 1226 are supported within the support tube 1222. Retaining ring 1242 may, for example, be a circumferentially split ring of known type.

During assembly of shell 1200, bearings 1228 and coupler shaft 1226 are first assembled and then positioned in the support tube 1222. Once in place, the retaining ring 1242 is seated in the groove 1240 to axially support the bearings 11228 and coupler shaft 1226 within support tube 1222. The coupler shaft 1226 is thus supported by the bearings 1228 for rotation relative to the support tube 1222 during operation of bone cleaning system 1040.

A receiver head 1244 is located at a lower end of the coupler shaft 1226 below retaining ring 1242. The receiver head 1244 is mounted and rotatably fixed to the axially lower end of coupler shaft 1226. Receiver head 1244 can be mounted to the coupler shaft 1226 by being threaded or welded thereto, or by another suitable means facilitating their rotating in unison. When shell 1200 is received in void space 64 of pedestal 58, receiver head 1244 engages the spindle head 90. Driving torque is transferred from the spindle head 90 to the coupler shaft 1226 through the receiver head 1244.

Receiver head 1244 has a downwardly directed face with recesses having corresponding shapes and locations that cooperate with those of the alignment pin 92 and the drive teeth 94 protruding upwardly from the top surface of the spindle head 90. More particularly, receiver head 1244 includes a centrally located alignment pin recess 1246 and four circumferentially and equiangularly spaced apart drive tooth-receiving recesses 1248. Recesses 1246, 1248 mate with alignment pin 92 and drive teeth 94, respectively. The walls of each drive tooth recess 1248 are parallel to the respectively interfacing surfaces of the drive tooth 94 slidably received therein. Spindle head 90 and receiver head 1244 thus define a dog clutch for transferring torque from the spindle head 90 to the receiver head 1244 when shell 1200 is received in void space 64 of pedestal 58, and teeth 94 and recesses 1248 are mated. In the embodiment shown, the spindle 90 can be raised as needed to mate with the receiver head 1244.

Shell 1200 includes a containment ring 1250 that is mounted to the base plate 1216. Containment ring 1250 has a semi-cylindrical wall with an outer diameter coincident with the outer diameter of base lower wall 1210. Containment ring 1250 extends upwardly from the base plate 1216. Containment ring 1250 has an inner semi-cylindrical surface 1252 that partially defines the shell void space 1202. The semi-cylindrical surface 1252 of containment ring 1250 is coaxial with central axis A10 of shell 1200.

Cutter 1048 is located within shell void space 1202. The cutter 1048 is supported by shell base 1208 to rotate about shell central axis A10. The cutter 1048 has an axially lower stub shaft 1254 with a D-shaped cross section that fits within a cooperating D-shaped axial bore (not separately numbered) in the axially upper section of tubular coupler shaft 1226. The lower stub shaft 1254 of cutter 1048 has one flat 1256 that forms its D-shaped cross section. Owing to the non-circular geometry of the D-shaped cross sections of lower stub shaft 1254 and its receiving bore in coupler shaft 1226, the cutter 1048 and coupler shaft 1226 are angularly fixed about axis A10 for rotation together. The cutter 1048 and coupler shaft 1226 rotate from 100 to 500 RPM.

Cutter 1048 also has an axially upper stub shaft 1258. A shaving rotor 1260 of the cutter 1048 is located axially intermediate the lower 1254 and upper 1258 stub shafts. The shaving rotor 1260 is generally cylindrical and has an outer diameter that is larger than the diameters of the lower 1254 and upper 1258 stub shafts. The shaving rotor 1260, upper stub shaft 1258, and lower stub shaft 1254 are integrally formed.

Shaving rotor 1260 includes helical flutes 1262 having cutting edges 1264. During operation of system 1040, cutter 48 rotates about the central axis A10 and the cutting edges 1264 clean bone stock in the shell void space 1202 by cutting soft tissue from the bone stock. Cutter 1048 rotates in a counterclockwise direction about axis A10 (as viewed from above).

A shaving tube 1270 extends coaxially about the shaving rotor 1260 of cutter 1048. Shaving tube 1270 defines a pair of diametrically opposed cutter windows 1272 through which tissue attached to the bone stock is received for engagement by the cutter 1048. Each cutter window 1272 is bounded by at least one shaver edge 1274. The shaver edges 1274 are sharp so as to cut soft tissue caught between the shaving rotor 1260 of cutter 1048 and the shaving tube 1270 when the shaving rotor 1260 rotates relative to the shaving tube 1270. The shaver edges 1274 also act as impingement structures against which soft tissue abuts and is temporarily held to facilitate cutting by shaving rotor 1260 of cutter 1048.

Bearing 1276 is located between upper stub shaft 1258 of cutter 1048 and shaving tube 1270. Another bearing 1278 is located between lower stub shaft 1254 of cutter 1048 and the shaving tube 1270. Bearings 1276, 1278 allow for relative rotation between the shaving tube 1270 and the cutter 1048.

In the embodiment shown, shaving tube 1270 is rotated about axis A10 by a drive belt 1280. Shaving tube 1270 has a driven pulley 1282 integrated into shaving tube upper end. A belt drive shaft 1284 is journaled in the base plate 1216 by a bearing 1286. A belt driving pulley 1288 is coaxially mounted on upper end of belt drive shaft 1284. The drive belt 1280 is taughtly disposed around driven pulley 1282 and driving pulley 1288. Shaving tube 1270 is rotated about axis A10 via the drive belt 1280 when the belt drive shaft 1284 is actuated.

A drive assembly 1400 actuates the belt drive shaft 1284. The drive assembly 1400 includes the receiver head 1244 and a gear train 1402. Receiver head 1244 acts as a torque input for the gear train 1402 of the drive assembly 1400. More particularly, the receiver head 1244 transfers torque from the drive spindle 86 to the gear train 1402. In certain embodiments, the receiver head 1244 has outer gear teeth (not illustrated). The gear train 1402 operatively interconnects the gear teeth of receiver head 1244 to belt drive shaft 1284 to transfer torque from the receiver head 1244 to the belt drive shaft 1284.

The gear train 1402 is configured so that the shaving tube 1270 rotates about axis A10 between 0 and 360 degrees once every 1 to 5 seconds and in alternating clockwise and counterclockwise directions. Oscillating movement of the shaving tube 1270 helps to dislodge and release bone stock caught between the shaving rotor 1260 and shaving tube 1270. Constant or periodic oscillation of shaving tube 1270 about axis A10 could be employed. Alternatively, constant or periodic rotation of shaving tube 1270 in the same direction could be employed to dislodge trapped bone stock. The gear train 1402 can be configured for any of these scenarios, or any combination thereof. Mechanisms by which continuous rotating input motion in a single direction is converted to an oscillating angular output motion may be incorporated into the gear train 1402. Such mechanisms include quick return or bell crank mechanisms, which are well known to those of ordinary skill in the art.

Shaving tube 1270 rotates, either in the same direction or opposite directions at about 30 to 120 RPM. Owing to the helical geometry of flutes 1262, and the relatively slow rotation of shaving tube 1270 compared to cutter 1048, as the cutter 1048 rotates cut soft tissue is augered axially upwardly along cutter 1048 between the cutter 1048 and the shaving tube 1270.

Two diametrically opposed debris windows 1290 are formed in shaving tube 1270. Debris windows 1290 are located above and are axially spaced from the cutter windows 1272. Debris windows 1290 are also circumferentially arranged at a 90 degree offset about axis A10 from the cutter windows 1272. Soft tissue that is cut from the bone stock during processing and augered axially upwardly along shaving tube 1270 by shaving rotor 1260 exits through the debris windows 1290.

A deflector ring 1292 is captured between bearing 1276 and shaving rotor 1260 to deflect the cut and augered soft tissue out of the shaving tube 1270 through the debris windows 1290. The deflector ring 1292 is coaxial with cutter 1048 and has a frustoconical outer surface 1294 with its diameter increasing from bottom to top. The outer surface 1294 provides a deflection surface against which the soft tissue being augered upwardly is urged radially outwardly and through the debris windows 1290.

At the top of the deflector ring 1292 the diameter of the outer surface 1294 is the same as or slightly smaller than the outer diameter of bearing 1276. At the bottom of the deflector ring 1292 the diameter of the outer surface 1294 is smaller than the major diameter of the shaving rotor 1260 defined by the cutting edges 1264 at the radially outer edges of the flutes 1262. This bottom diameter of deflector ring 1292 is the same as the minor diameter of shaving rotor 1260 defined by the radially innermost surfaces of cutter flutes 1262.

Debris catches 1296 receive from debris windows 1290 cut soft tissue that has been augered upwardly along the shaving rotor 1260 between the cutter 1048 and the shaving tube 1270. The augered and deflected soft tissue is collected on the debris catches 1296 for later use or disposal.

A circular tumble plate 1298 is rotatably fixed to the coupler shaft 1226. The bone stock sits on top of the tumble plate 1298 during cleaning so that, when actuated, the tumble plate 1298 carries the bone stock to and from the cutter 1048. Referring to FIG. 31, tumble plate 1298 has a central, D-shaped aperture 1300 that cooperates with D-shaped cross section of lower stub shaft 1254 that extends therethrough. The cooperation between the D-shaped stub shaft 1254 and central tumble plate aperture 1300 rotatably fixes the tumble plate 1298 to the cutter 1048. During assembly, the D-shaped cross section passes through the D-shaped center aperture 1300 of tumble plate 1298 and into cooperating D-shaped bore in coupler shaft 1226. Cutter 1048, tumble plate 1298, and coupler shaft 1226 are thus rotatably fixed together for simultaneous rotation. During operation of system 1040, tumble plate 1298 is thus driven about the central axis A10 by coupler shaft 1226.

The upper surface 1301 of the tumble plate 1298 carries the bone stock. In the embodiment shown, the upper surface 1301 is flat and smooth. In some embodiments, the upper surface 1301 is textured or has gripping features (not illustrated) to grip the bone stock and facilitate moving the bone stock to the cutter 1048.

An arm 1302 extends over the planar upper surface of tumble plate 1298. When it is actuated, the arm 1302 moves across the tumble plate 1298 between disengaged and engaged positions. In an extreme clockwise position, the arm 1302 is generally located along a periphery of the circular tumble plate 1298.

Figure 33:
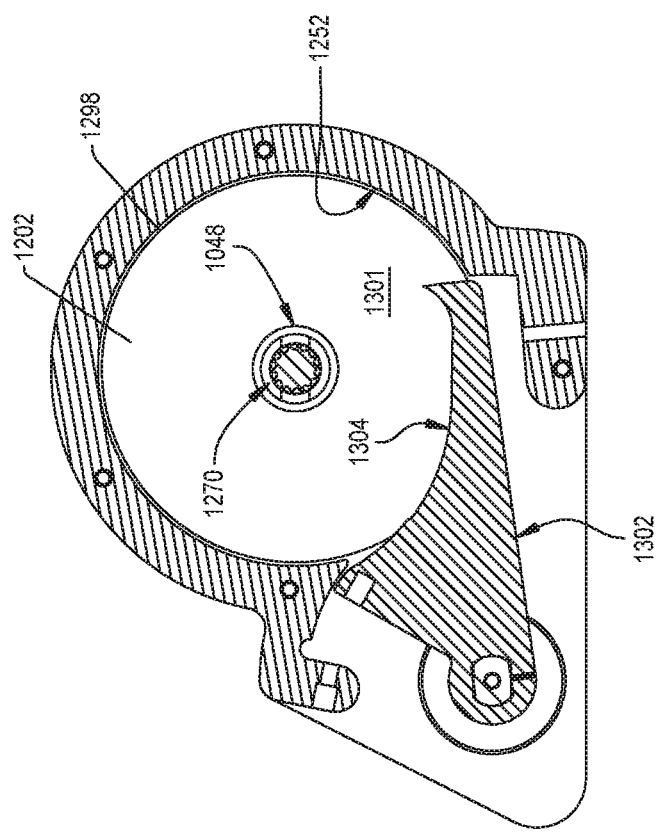
FIG. 33 is a cross-sectional top view of an arm and a containment ring of the alternative cleaning module.

FIG. 33 shows arm 1302 in a disengaged position. Arm front face 1304 is oriented so that, in a disengaged position, the front face 1304 cooperates with the inwardly directed arcuate surface 1252 of the containment ring 1250 to further define the shell void space 1202. The arm front face 1304 forms a nearly continuous surface with the inwardly directed arcuate surface 1252 of containment ring 1250 when in the disengaged position. When the arm 1302 is out of this disengaged position and moving toward the cutter 1048 it diverts bone stock on the rotating tumble plate 1298 toward the rotating cutter 1048.

FIGS. 34 and 35 show arm 1302 in an engaged position (bone stock not shown). When the arm 1302 is in an engaged position, the front face 1304 guides bone stock toward the shaving rotor 1260 of cutter 1048 through the windows 1272 in shaving tube 1270. More particularly, bone stock carried by the tumble plate 1298 is diverted by arm front face 1304 toward the cutting edges 1264 of cutter 1048. Arm front face 1304 acts as a bearing surface that presses bone stock into windows 1272 and against the cutting edges 1264.

Referring specifically to FIG. 35, the front face 1304 abuts cylindrical outer surface 1377 of the shaving tube 1270 when the arm 1302 is in this engaged position. In versions where the shaving tube 1270 rotates, the cylindrical outer surface 1377 of the shaving tube 1270 is in constant abutting contact with the front face 1304 to prevent the arm 1302 from intruding on the cutter 1048 and to maintain a gap or spacing between the front face 1304 and the cutter 1048.

When arm front face 1304 engages or is at least in close proximity to shaving tube 1270, but after some amount of bone cleaning takes place, shaving tube 1270 may be rotated about axis A10 to dislodge bone stock trapped therein. The arm 1302 provides a bearing surface against which trapped bone stock can bear as it is loosened or dislodged from cutter 1048 and/or shaving tube 1270 when the shaving tube 1270 rotates.

Referring to FIG. 36, arm 1302 includes a hub 1305 pivotally mounted to base plate 1216. Hub 1305 is supported on pivot shaft 1306 for pivotal movement between disengaged and engaged positions. The hub 1305 fits over pivot shaft 1306. Pivot shaft 1306 has a radially extending annular flange 1308. Pivot shaft upper body 1310 extends upwardly from the flange 1308 into downwardly open bore 1312 in arm hub 1305. Fastener 1314 locks the hub 1305 to the pivot shaft 1306. Fastener 1314 has a head (not separately numbered) that sits in a counter bore 1316 in hub 1305. Fastener 1314 further includes a threaded shaft (not separately numbered) depending downwardly from the fastener head. The threaded shaft extends into bore 1318 defined in hub 1305 below counter bore 1316. Pivot shaft upper body 1310 has a threaded central bore (not separately numbered) into which is received the threaded shaft of fastener 1314 to fix arm 1302 to pivot shaft 1306.

Bearing 1320 is seated in a counter bore (not separately numbered) in the base plate 1216. Downwardly-facing annular shoulder of pivot shaft flange 1308 axially abuts bearing 1320 in the base plate 1216. A spacer 1322 surrounds pivot shaft upper body 1310 and is located between the arm 1302 and the upwardly-facing annular shoulder of the pivot shaft flange 1308. Spacer 1322 keeps arm 1302 spaced from the upper surface 1301 of tumble plate 1298. Pivot shaft 1306 has a lower body 1324 supported in bearing 1320 that extends through the counter bore in the base plate 1216. Induced rotation of the pivot shaft lower body 1324 imparts reversible pivoting motion of arm 1302 between its disengaged and engaged positions.

Pivot shaft upper body 1310 and bore 1312 of arm 1302 have complimentary non-circular shapes that cooperate to rotatably fix pivot shaft 1306 and hub 1305. More particularly, they are each provided with diametrically opposed flats, as shown in FIGS. 31 and 39. Pivot shaft 1306 and arm 1302 are thus angularly fixed for rotating in unison.

Pivot shaft 1306 is operatively connected to the gear train 1402. Gear train 1402 transfers torque received from base unit motor 44 through receiver head 1244 to pivot shaft 1306. Arm 1302 pivots upon actuation of pivot shaft 1306 by gear train 1402. The gear train 1402 can include mechanisms for transferring torque from the receiver head 1244 to the arm 1302 to reciprocate the arm between engaged and disengaged positions such as a quick-return mechanism or sliding crank mechanism.

The gear train 1402 is configured to limit the force provided by the front face 1304 of arm 1302 against the bone stock such that only soft tissue is cut from the bone stock without damaging the periosteum layer. The force can be limited by a force limiting clutch or other feature/mechanism in the gear train 1402. The force limiting feature is associated with the arm 1302 so that the force with which the arm 1302 presses bone stock into the cutter 1048 can be limited.

Arm 1302 is periodically reciprocated by the gear train 1402 between engaged and disengaged positions to reorient the bone stock trapped between the arm 1302 and the shaving tube 1270. The arm 1302 pivots between the engaged and disengaged positions about 5 to 20 times per minute. The speed at which the arm 1302 pivots between the engaged and disengaged positions is from 5 to 20 RPM. Movement of the arm 1302 may be timed to the speed/motion of the shaving tube 1270 so that the arm 1302 is in the engaged position when the shaving tube 1270 is actuated.

Referring to FIGS. 37-39, the arm 1302 has generally planar top 1326 and bottom 1328 surfaces. The arm hub 1305 has a semi-cylindrical or arcuate outer surface 1330 defined between the top 1326 and bottom 1328 surfaces. The arm 1302 further includes planar rear 1332 and side 1334 faces defined between the top 1326 and bottom 1328 surfaces. The rear 1332 and side 1334 faces intersect the arcuate outer surface 1330. The rear face 1332 and side face 1334 are spaced from one another.

Rear face 1332 and side face 1334 lie in planes P1, P2, respectively, that are substantially transverse to one another. The planes P1, P2 lie at an acute angle α to one another. Spacing between the rear face 1332 and side face 1334 increases as the faces 1332, 1334 extend further away from the hub 1305.

Arm front face 1304 is arcuate in shape and is defined between the top 1326 and bottom 1328 surfaces. The front face 1304 faces the cutter 1048. A first edge 1336 of arm 1302 is formed at an intersection of the front face 1304 and the side face 1334. The front face 1304 extends from the first edge 1336 to a terminus edge 1338. The terminus edge 1338 is formed at an intersection of end surface 1339 and front face 1304. The arm 1302 in its engaged position adjacent the shaving tube 1270 defines an inwardly directed path along which the bone stock on the rotating tumble plate 1298 is guided towards the center of shell void space 1202 and the cutter 1048.

Referring to FIGS. 40-41, containment ring 1250 has a semi-cylindrical or arcuate wall 1340 that extends more than 180 degrees concentrically about axis A10. First 1342 and second 1344 wings are integrally formed at each end of the wall 1340. First wing 1342 is shaped to define a recess 1346 that receives a distal end of arm 1302 in a disengaged position. Second wing 1344 is shaped to define a recess 1348 that receives a proximal end of arm 1302 in an engaged position.

Each wing 1342, 1344 has a threaded through bore 1350, 1352 for threaddedly receiving a set screw 1354, 1356. Set screws 1354, 1356 extend through its threaded bore 1350, 1352 in containment ring 1250 and into its recess 1346, 1348, respectively. The set screws 1354, 1356 are adjustable in bores 1350, 1352 to adjust a gap between the arm 1302 and the wings 1342, 1344, and tune the extreme positions of the arm 1302 by adjusting the stop position of the arm 1302 in extreme clockwise and counterclockwise positions. Set screws 1354 and 1356 abut arm rear face 1332 and side faces 1334 to adjust and tune the extreme arm clockwise and counterclockwise positions, respectively, of the arm 1302. The terminal ends of the set screws 1354, 1356 act as stops for the arm 1302 to prevent its over rotation into recesses 1346, 1348 as it moves into its disengaged and engaged positions, respectively. In the extreme counterclockwise position arm 1302 is tuned so that front face 1304 is in contact with or nearly in contact with shaving tube 1270. In the extreme clockwise position arm 1302 is tuned so that front face 1304 is flush with or nearly flush with inner cylindrical surface 1252 of containment ring 1250.

Threaded bores 1360 are formed axially through the arcuate wall 1340 and wings 1342, 1344 and mate with clearance bores (not illustrated) in base plate 1216 and lower wall 1210. Threaded fasteners (not illustrated) are received from beneath into the clearance bores and the threaded bores 1360 to attach the shell base lower wall 1210 and containment ring 1250 to the base plate 1216.

Figure 42:
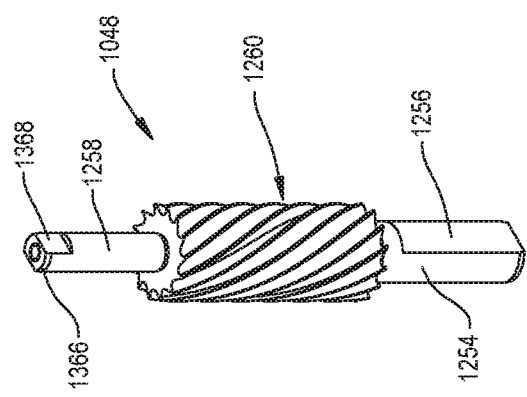
FIG. 42 is a perspective view of a cutter of the alternative cleaning module.
Figure 43:
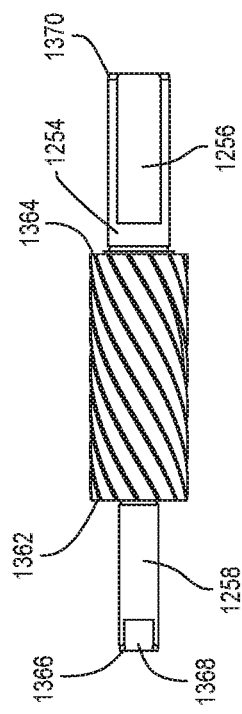
FIG. 43 is a side view of the cutter of the alternative cleaning module.
Figure 44:
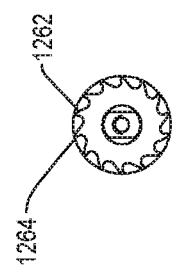
FIG. 44 is an end view of the cutter of the alternative cleaning module.

As shown in FIGS. 42-44, fourteen flutes 1262 and corresponding cutting edges 1264 are defined on shaving rotor 1260. Upper 1362 and lower 1364 axial ends of shaving rotor 1260 are flat and lie in planes perpendicular to axis A10. Flutes 1262 and cutting edges 1264 extend between the ends 1362, 1364. The flutes 1262 and cutting edges 1264 are arranged such that they helically wrap less than 180 degrees about shaving rotor 1260 between ends 1362, 1364. The cutting edges each have a rake angle of between 0 and 10 degrees and more preferably have a rake angle of 7 degrees.

Cutter upper stub shaft 1258 extends upwardly from shaving rotor 1260 to a chamfer 1366. Diametrically opposed flats 1368 are defined at an upper end of upper stub shaft 1258 through chamfer 1366. Upper stub shaft 1258 is smooth and generally cylindrical between flats 1368 and shaving rotor 1260. Cutter lower stub shaft 1254 extends downwardly from shaving rotor 1260 to a chamfer 1370. Lower stub shaft 1254 is smooth and generally cylindrical between flat 1256 and shaving rotor 1260.

Figure 46:
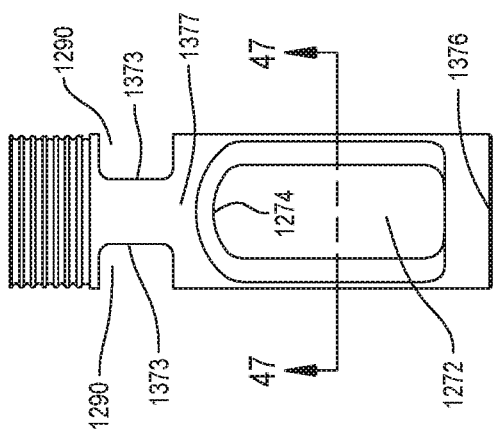
FIG. 46 is a side view of the shaving tube of the alternative cleaning module.
Figure 47:
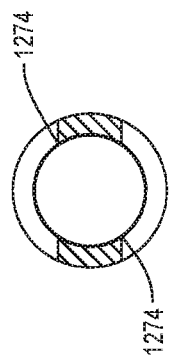
FIG. 47 is a cross-sectional view of the shaving tube taken generally along line 47-47 in FIG. 46.
Figure 45:
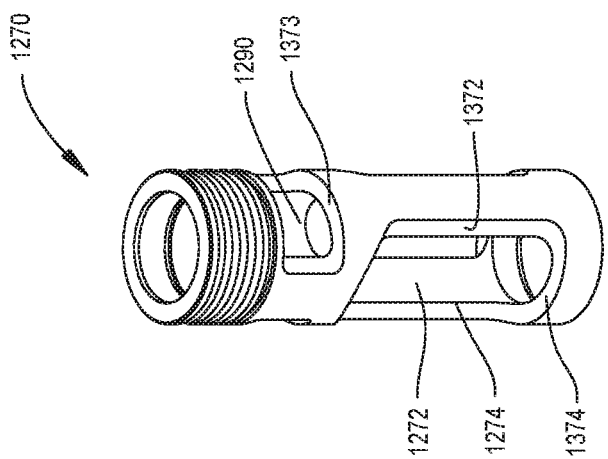
FIG. 45 is a perspective view of a shaving tube of the alternative cleaning module.

Referring to FIGS. 45-47, shaving tube 1270 is generally cylindrical for fitting over cutter 1048. As shown in FIG. 45, the shaving tube 1270 has diametrically opposed cut-outs 1372 formed in its cylindrical wall (not separately numbered) that define the cutter windows 1272. Cut-outs 1373 are also formed in the shaving tube wall to define the debris windows 1290.

Cut-outs 1372 create the sharp shaver edges 1274 that cut soft tissue entering cutter windows 1272. A shaver edge 1274 is located on both sides and the top of each cutter window 1272. Thus, the shaver edges 1274 further define the top and sides of the cutter windows 1272. Sills 1374 at the bottoms of the shaving tube windows 1272 formed by the cut-outs 1372 are generally flat and parallel with the upper surface 1301 of the tumble plate 1298.

In the shown embodiment, the cut-out edges of each cutter window 1272 form a continuous shaver edge 1274. However, in alternative embodiments, separate and distinct shaver edges may be provided along the sides and top of each window 1272. The shaver edges 1274 are located so that soft tissue trapped between shaving rotor 1260 and the inner cylindrical wall of shaving tube 1270 is cut by the shaver edges 1274 either at the sides or at the top of the cutting windows 1272.

A base 1376 of the shaving tube 1270 is located below the cutter windows 1272. In versions where the shaving tube 1270 rotates, the cylindrical outer surface 1377 of the shaving tube 1270 is in constant abutting contact with the front face 1304 of arm 1302 via the base 1376 to maintain a gap or spacing between the front face 1304 and the cutter 1048.

Referring to FIGS. 48-50, the debris catches 1296 include arcuate mounts 1378 by which the debris catches 1296 are attached to the shaving tube 1270. As best shown in FIG. 48, the arcuate mounts 1378 include tube halves 1380. Tube halves 1380 mate with one another to form an outer tube structure (not separately numbered) located coaxially about shaving tube 1270. Mounts 1378 have male projections 1382, 1383 that extend from the tube halves 1380 and mating female notches 1384, 1385 recessed in the tube halves 1380. The male and female mating projections 1382, 1383 and notches 1384, 1385 engage one another to align the tube halves 1380 and form the outer tube structure. The mating features 1382, 1383, 1384, 1385 and tube halves 1380 are secured to one another by adhesive, fasteners, or the like.

Referring to FIG. 49, debris windows 1392 are formed in each tube half 1380. The debris windows 1392 are aligned with the shaving tube debris windows 1290. More particularly, alignment protrusions 1387 act to align the windows 1290, 1392. Alignment protrusions 1387 extend inwardly from a semi-cylindrical inner surface of tube halves 1380 on each side of the debris windows 1392. Alignment protrusions 1387 are dimensioned and shaped for receipt into the shaving tube debris windows 1290 adjacent the opposite side edges of the cutouts 1373. The protrusions 1387 provide axial alignment of the windows 1290, 1392 their opposite ends abutting the opposite top and bottom edges of cutouts 1373. Protrusions 1387 provide radial alignment of the windows 1290, 1392 by their abutting contact with the respective side edges of cutouts 1373.

Catch trays 1386 are attached to each arcuate mount 1378 below debris windows 1392. Cut soft tissue that has been augered along the interior of the shaving tube 1270, and deflected by deflector ring 1292 radially outwardly through debris windows 1290 passes through aligned debris windows 1392 and is deposited onto the catch trays 1386 where the soft tissue and other debris is ultimately collected. Each catch tray 1386 includes a bottom 1388 and a peripheral wall 1390 extending upwardly from the bottom 1388. Peripheral wall 1390 holds and contains the soft tissue and other debris deposited on the bottom 1388.

Figure 30:
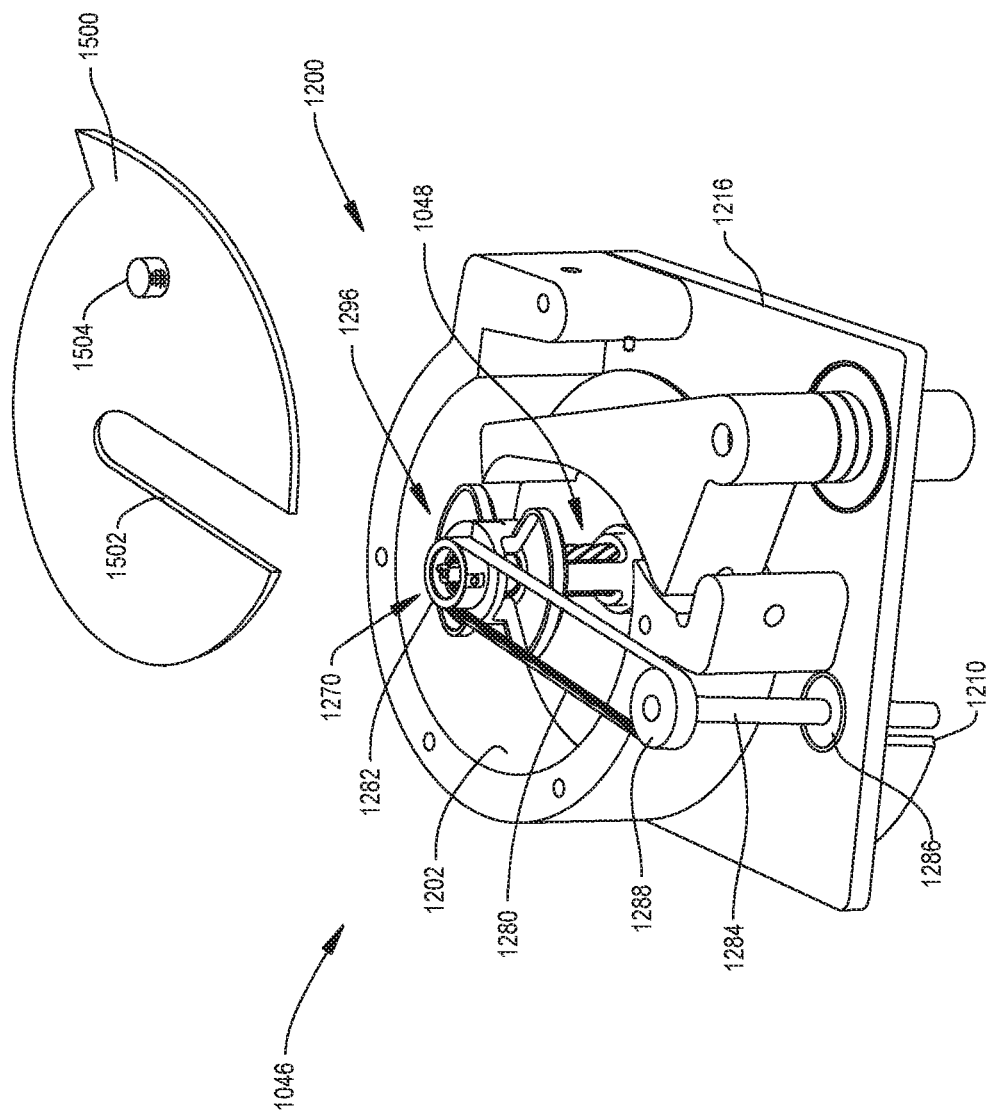
FIG. 30 is a perspective view of an alternative cleaning module.

A lid 1500 is removably positionable on top of the containment ring 1250 of shell 1200 (see FIG. 30). The lid 1500 covers the shell void space 1202 and the bone stock being cleaned. The lid 1500 has a slot 1502 for accepting the shaving tube 1270 when sliding the lid 1500 in place over the shell void space 1202. A handle 1504 is fixed to the lid 1500. Handle 1504 extends upwardly from the lid 1500 to be grasped by the user. The user can slide the lid in place over the containment ring 1250 and beneath the debris catches 1296 or remove the lid 1500 using the handle 1504.

During operation, uncleaned bone is first placed in the shell void space 1202 for cleaning and the lid 1500 is then slid into place atop containment ring 1250 to cover the void space 1202. Fasteners (not illustrated) may be used to fasten the lid 1500 to the containment ring 1250 via threaded bores 1360. The uncleaned bone includes soft tissue attached thereto that requires removal without damaging the periosteum layer.

The alternative cleaning module 1046 is then fitted to the base unit 42. The surgical personnel actuate the alternative cleaning module 1046 by depressing the push button of base unit switch 98. In response to the depression of switch 98 the motor controller (not illustrated) causes power to be applied to the motor 44, which energizes the motor 44 and causes its output shaft 78 to turn in a direction that drives rotation of cutter 1048 counterclockwise as viewed from above.

The tumble plate 1298 rotates in unison with the cutter 1048 in the counterclockwise direction. Tumble plate 1298 operates to carry the bone stock toward the front face 1304 of arm 1302 when the arm is out of its disengaged position. In the engaged position, arm front face 1304 guides the bone stock toward shaving tube 1270 and the cutter shaving rotor 1260 to cut soft tissue from the bone stock.

Cutting edges 1264 of shaving rotor 1260 and/or shaver edges 1274 of shaving tube 1270 cut away soft tissue from bone. The cut soft tissue and other debris is then augered upwardly between the shaving rotor 1260 and shaving tube 1270. The augered tissue is deflected radially outwardly by deflector ring 1292 into and through the debris windows 1290 in shaving tube 1270 and windows 1392 in each tube half 1380. The tissue is then collected onto catch trays 1386 for disposal. This provides a separation of soft tissue and other debris from the remaining bone of the bone stock.

After some amount of bone cleaning takes place, drive assembly 1400 rotates shaving tube 1270 about axis A10 to dislodge bone stock trapped therein. The arm 1302 provides a bearing surface against which trapped bone stock can bear as it is loosened or dislodged from cutter 1048 and/or shaving tube 1270 when the shaving tube 1270 rotates. The gear train 1402 is configured so that the shaving tube 1270 rotates about axis A10 between 0 and 360 degrees once every 1 to 5 seconds and in alternating clockwise and counterclockwise directions.

During cleaning, drive assembly 1400 periodically pivots arm 1302 between engaged and disengaged positions to reorient the bone stock trapped between the arm 1302 and the shaving tube 1270. The arm 1302 pivots between the engaged and disengaged positions about 5 to 20 times per minute. This further facilitates removal of soft tissue and debris from all surfaces of the bone stock.

Once the alternative cleaning module 1046 has sufficiently removed soft tissue from the bone, the lid 1500 is removed. The catch trays 1386, and soft tissue/debris collected in the catch trays 1386 are removed and discarded. Next, the cleaned bone is grabbed by forceps or other device (not illustrated) for further processing. At the conclusion of the cleaning process, the alternative cleaning module 1046 is removed from the base unit 42. The alternative cleaning module 1046 may then be cleaned or discarded.

Obviously many modifications and variations of the present invention are possible in light of the above description. While this description is directed to particular embodiments, it is understood that those skilled in the art may conceive of modifications and/or variations to the specific embodiments shown and described herein. Any such modifications or variations, which fall within the purview of this description, are intended to be included herein as well. It is understood that the description herein is intended to be illustrative only and is not intended to be limited.

What is claimed is:

1. A bone cleaning assembly, said assembly including:
a shell defining a void space for receiving bone stock;
a cutter formed with a plurality of cutting edges and a shaving tube disposed around said cutter, said cutter is rotatably mounted to said shell so as to be disposed in said shell to remove tissue from bone stock received therein;
a lid defining a collection surface onto which cut tissue collects; and
a cap removably coupled to said shell to cover and enclose said collection surface, wherein said cap and said collection surface cooperate to define a collecting space for soft tissue;
wherein said cutter and shaving tube cooperate to auger cut tissue axially upward to collect on said collection surface.

2. The assembly as set forth in claim 1, wherein said cutter is formed to have a plurality of flutes that define said plurality of cutting edges.

3. The assembly as set forth in claim 2, wherein said plurality of flutes and said plurality of cutting edges helically wrap about a shaving rotor.

4. The assembly as set forth in claim 3, wherein said plurality of flutes and said plurality of cutting edges each have a helix angle of from 20 to 70 degrees and/or said plurality of cutting edges each have a rake angle of between −10 and 10 degrees.

5. The assembly as set forth in claim 1, wherein said shaving tube comprises a window and at least one shaving edge at least partially defines said window.

6. The assembly as set forth in claim 1, wherein said lid comprises a slide moveably mounted thereto, wherein a user can slide said lid to uncover an opening in said shell through which bone stock to be cleaned can be placed in said void space and cleaned bone stock can be removed from said void space.

7. The assembly as set forth in claim 1, wherein the collection surface is spaced below a top end of the shaving tube to act as a debris catch.

8. The assembly as set forth in claim 1 further comprising a closed containment wall within said void space, said closed containment wall moveably mounted to said shell so that said containment wall is able to move between a disengaged and an engaged position to corral bone stock so that bone stock is trapped and pressed into said cutter.

9. The assembly as set forth in claim 1 further comprising a guide configured to move bone stock received in said void space toward said cutter.

10. A bone cleaning assembly, said assembly including:
a shell defining a void space for receiving bone stock;
a cutter comprising a shaving rotor having a plurality of helically wrapped flutes that define a plurality of cutting edges, said cutter is rotatably mounted to said shell;
a shaving tube extending coaxially around said cutter and comprising a window and at least one shaving edge that at least partially defines said window;
a space between the cutter and the shaving tube that acts as a passage through which soft tissue cut from bone stock is augured and expelled whereby the void space is in communication with a collection space; and
a closed containment wall within said void space, said closed containment wall moveably mounted to said shell so that said containment wall is able to move between a disengaged and an engaged position to corral bone stock so that bone stock is trapped and pressed into said cutter.

11. The assembly as set forth in claim 10 further comprising a lid defining a collection surface onto which cut tissue collects.

12. The assembly as set forth in claim 11, wherein said lid comprises a slide moveably mounted thereto, wherein a user can slide said lid to uncover an opening in said shell through which bone stock to be cleaned can be placed in said void space and cleaned bone stock can be removed from said void space.

13. The assembly as set forth in claim 11 further comprising a cap removably coupled to said shell to cover and enclose said collection surface, wherein said cap and said collection surface cooperate to define a collecting space for soft tissue.

14. The assembly as set forth in claim 10, wherein said plurality of flutes and said plurality of cutting edges each have a helix angle of from 20 to 70 degrees and/or said plurality of cutting edges each have a rake angle of between −10 and 10 degrees.

15. The assembly as set forth in claim 10 further comprising a guide configured to move bone stock received in said void space toward said cutter.

16. A bone cleaning assembly, said assembly including:
a shell defining a void space for receiving bone stock;
a cutter formed with a plurality of cutting edges and a shaving tube disposed around said cutter, said cutter is rotatably mounted to said shell so as to be disposed in said shell to remove tissue from bone stock received therein;
a lid defining a collection surface onto which cut tissue collects;
wherein said cutter and shaving tube cooperate to auger cut tissue axially upward to collect on said collection surface; and
wherein the collection surface is spaced below a top end of the shaving tube and above a bottom end of the shaving tube to act as a debris catch, and wherein the collection surface surrounds the shaving tube.

17. The assembly as set forth in claim 16, wherein said cutter is formed to have a plurality of flutes that define said plurality of cutting edges.

18. The assembly as set forth in claim 17, wherein said plurality of flutes and said plurality of cutting edges helically wrap about a shaving rotor.

* * * * *